(12) United States Patent
Murooka et al.

(10) Patent No.: US 10,922,805 B2
(45) Date of Patent: Feb. 16, 2021

(54) MICRONEEDLE ARRAY IMAGING DEVICE, MICRONEEDLE ARRAY IMAGING METHOD, MICRONEEDLE ARRAY INSPECTION DEVICE, AND MICRONEEDLE ARRAY INSPECTION METHOD

(71) Applicant: FUJIFILM Corporation, Tokyo (JP)

(72) Inventors: Takashi Murooka, Kanagawa (JP); Kazuo Onishi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 95 days.

(21) Appl. No.: 16/283,841

(22) Filed: Feb. 25, 2019

(65) Prior Publication Data

US 2019/0188844 A1 Jun. 20, 2019

Related U.S. Application Data

(63) Continuation of application No. PCT/JP2017/029528, filed on Aug. 17, 2017.

(30) Foreign Application Priority Data

Sep. 6, 2016 (JP) ................................ 2016-173484

(51) Int. Cl.
*G06T 7/00* (2017.01)
*G01N 21/95* (2006.01)
(Continued)

(52) U.S. Cl.
CPC ........... *G06T 7/0002* (2013.01); *A61M 37/00* (2013.01); *A61M 37/0015* (2013.01);
(Continued)

(58) Field of Classification Search
CPC .. G06T 7/0002; G01N 21/95; G01N 21/8806; G01N 21/958; G01N 2021/8841;
(Continued)

(56) References Cited

U.S. PATENT DOCUMENTS

2008/0287858 A1 11/2008 Duan
2009/0086197 A1* 4/2009 Fukuda .............. G01N 21/8806
356/239.7
(Continued)

FOREIGN PATENT DOCUMENTS

JP H1164232 3/1999
JP 2010071845 4/2010
(Continued)

OTHER PUBLICATIONS

Takehiko et al, JP2016-166769 (A), "Method of Inspecting MicroNeedles", machine translated version, pp. 1-29. (Year: 2016).*
(Continued)

*Primary Examiner* — Yon J Couso
(74) *Attorney, Agent, or Firm* — JCIPRNET

(57) ABSTRACT

Provided are a microneedle array imaging device, a microneedle array imaging method, a microneedle array inspection device, and a microneedle array inspection method which enable inspection of a microneedle array with high accuracy based on an obtained image. A microneedle array 1 is imaged from a side of a surface on which microneedles 2 are arranged by irradiating a surface on a side opposite to the surface on which the microneedles 2 are arranged with parallel light as illumination light. At this time, the surface is irradiated with the illumination light under conditions in which an incident angle α of light onto a bottom surface 2a of the microneedle 2 is 90−θ° or greater and an incident angle β of light onto a side surface 2b of the microneedle 2 is less than a critical angle γ. In this manner, a state in which almost no light is emitted from a tip portion of the microneedle 2 can be generated. As the result, an image in which only the tip portion of the microneedle 2 is dark and other portions, in other words, a base portion of the
(Continued)

microneedle 2 and a portion of a sheet 3 are bright can be imaged.

15 Claims, 12 Drawing Sheets

(51) Int. Cl.
*A61M 37/00* (2006.01)
*G01N 21/88* (2006.01)
*G01N 21/958* (2006.01)
*H04N 5/225* (2006.01)

(52) U.S. Cl.
CPC .......... *G01N 21/8806* (2013.01); *G01N 21/95* (2013.01); *G01N 21/958* (2013.01); *H04N 5/2256* (2013.01); *A61M 2037/0023* (2013.01); *A61M 2037/0061* (2013.01); *G01N 2021/8841* (2013.01)

(58) Field of Classification Search
CPC .............. A61M 37/00; A61M 37/0015; A61M 2037/0023; A61M 2037/0061; H04N 5/2256
See application file for complete search history.

(56) References Cited

U.S. PATENT DOCUMENTS

| | | | |
|---|---|---|---|
| 2009/0162798 A1* | 6/2009 | Tomono | G03F 7/201 430/320 |
| 2015/0126923 A1 | 5/2015 | Falo, Jr. et al. | |
| 2015/0306363 A1 | 10/2015 | Meyer et al. | |
| 2018/0250503 A1* | 9/2018 | Enomoto | A61M 37/00 |
| 2018/0272621 A1 | 9/2018 | Falo, Jr. et al. | |

FOREIGN PATENT DOCUMENTS

| | | |
|---|---|---|
| JP | 2011013065 | 1/2011 |
| JP | 2015515886 | 6/2015 |
| JP | 2016166769 | 9/2016 |

OTHER PUBLICATIONS

"International Search Report (Form PCT/ISA/210) of PCT/JP2017/029528," dated Nov. 7, 2017, with English translation thereof, pp. 1-5.

"Written Opinion of the International Searching Authority (Form PCT/ISA/237) of PCT/JP2017/029528," dated Nov. 7, 2017, with English translation thereof, pp. 1-9.

Office Action of Japan Counterpart Application, with English translation thereof, dated Jun. 25, 2019, pp. 1-10.

"Search Report of Europe Counterpart Application", dated Aug. 5, 2019, pp. 1-9.

"Office Action of Japan Counterpart Application," with English translation thereof, dated Oct. 7, 2019, pp. 1-4.

\* cited by examiner

MICRONEEDLE ARRAY IMAGING DEVICE, MICRONEEDLE ARRAY IMAGING METHOD, MICRONEEDLE ARRAY INSPECTION DEVICE, AND MICRONEEDLE ARRAY INSPECTION METHOD

CROSS-REFERENCE TO RELATED APPLICATIONS

The present application is a Continuation of PCT International Application No. PCT/JP2017/029528 filed on Aug. 17, 2017 claiming priority under 35 U.S.C § 119(a) to Japanese Patent Application No. 2016-173484 filed on Sep. 6, 2016. Each of the above applications is hereby expressly incorporated by reference, in their entirety, into the present application.

BACKGROUND OF THE INVENTION

1. Field of the Invention

The present invention relates to a microneedle array imaging device, a microneedle array imaging method, a microneedle array inspection device, and a microneedle array inspection method of imaging a microneedle array formed of a plurality of microneedles being arranged on a sheet and inspecting the microneedle array based on the obtained image.

2. Description of the Related Art

In recent years, a microneedle array has been attracting attention as new drug delivery means. A microneedle array has a structure in which a plurality of needle-like fine protrusions called microneedles are arranged on a sheet and is used by being attached to the skin surface. In other words, by attaching the microneedle array to the skin surface, a drug is infiltrated into the skin from the microneedles so that the drug is delivered into the body. From the viewpoint of efficiently delivering a drug to an affected area, the microneedle array is expected as new means for drug administration.

JP2010-071845A suggests a method of imaging a microneedle array under so-called dark field illumination and inspecting the microneedle array based on the obtained image, as a method of inspecting a microneedle array. Specifically, a microneedle array is irradiated with illumination light from a lateral direction, the microneedle array is imaged from directly above, and the microneedle array is inspected based on the obtained image.

SUMMARY OF THE INVENTION

However, in a case where a transparent or semitransparent microneedle array is imaged according to the method described in JP2010-071845A, there is a problem in that inspection with high accuracy is not able to be performed because the contrast of the obtained image becomes insufficient.

The present invention has been made in consideration of the above-described circumstances, and an object thereof is to provide a microneedle array imaging device, a microneedle array imaging method, a microneedle array inspection device, and a microneedle array inspection method which enable inspection of a microneedle array with high accuracy based on an obtained image.

The means for solving the above-described problems is as follows.

(1) A microneedle array imaging device comprising: an illumination unit which irradiates a surface on a side opposite to a surface on which a plurality of microneedles whose inclination angle of a side surface with respect to a bottom surface is $\theta°$ are arranged on a sheet to form a microneedle array, with parallel light as illumination light; and an imaging section which images the microneedle array from a side of the surface on which the microneedles are arranged, in which the illumination unit irradiates the surface with the illumination light under conditions in which an incident angle of light onto the bottom surface of the microneedle is $90-\theta°$ or greater and an incident angle of light onto the side surface of the microneedle is less than a critical angle.

According to the present aspect, the surface on a side opposite to the surface on which the microneedles forming the microneedle array are arranged is irradiated with illumination light. In addition, the microneedle array is imaged from a side of the surface on which the microneedles are arranged. Parallel light is used as the illumination light and the surface is irradiated under certain conditions. In other words, the surface is irradiated with the illumination light under conditions in which an incident angle of light onto the bottom surface of the microneedle is $90-\theta°$ or greater and an incident angle of light onto the side surface of the microneedle is less than a critical angle. In this manner, a state in which almost no light is emitted from a tip portion of the microneedle can be generated. As the result, an image in which only the tip portion of the microneedle is dark and other portions, in other words, a base portion of the microneedle and a portion of the sheet are bright can be imaged. Further, in this manner, the microneedle array can be inspected with high accuracy based on the obtained image. In other words, since an image with a high contrast can be obtained, the shape and the like of each microneedle can be inspected with high accuracy.

Further, the first condition, that is, the condition in which the incident angle of light onto the bottom surface of the microneedle is $90-\theta°$ or greater is a condition derived from the inclination angle of the side surface of the microneedle. In a case where the illumination light is incident on the bottom surface of the microneedle at an incident angle of less than $90-\theta°$, the illumination light is propagated to the tip of the microneedle. Therefore, the condition in which the incident angle of light on the bottom surface of the microneedle is $90-\theta°$ or greater is defined as the first condition.

The second condition, that is, the condition in which the incident angle of light onto the side surface of the microneedle is less than the critical angle is a condition for defining that the light incident inside from the bottom surface of the microneedle is not totally reflected on the side surface thereof. In a case where the light incident inside from the bottom surface of the microneedle is totally reflected on the side surface thereof, the light is easily propagated to the tip of the microneedle. Therefore, the condition in which light incident inside from the bottom surface of the microneedle is not totally reflected on the side surface thereof, in other words, the condition in which the incident angle of light onto the side surface of the microneedle is less than the critical angle is defined as the second condition. Further, the "incident angle of light onto the side surface of the microneedle" indicates an incident angle of light, which enters the inside of the microneedle from the bottom surface of the microneedle, advances the inside of the microneedle, and is incident on the side surface of the microneedle, onto the side surface of the microneedle.

Both conditions are conditions for making light difficult to enter the tip of the microneedle. By irradiating the surface with parallel illumination light such that two conditions described above are satisfied, an image in which only the tip portion of the microneedle is dark and other portions, in other words, a base portion of the microneedle and a portion of the sheet are bright can be imaged. In this manner, the microneedle array can be inspected with high accuracy based on the obtained image.

(2) The microneedle array imaging device according to (1), in which the illumination unit irradiates the surface with the illumination light under conditions in which an incident angle of light onto the bottom surface of the microneedle is 90−θ° or greater and an incident angle of light onto the side surface of the microneedle is less than 46°.

In a case of a typical microneedle array which mainly contains a water-soluble polymer, a state in which almost no light is emitted from the tip portion of the microneedle can be generated by irradiating the surface with illumination light under conditions in which the incident angle of light which is incident on the side surface of the microneedle is less than 46°. In this manner, an image in which only the tip portion of the microneedle is dark and other portions, in other words, a base portion of the microneedle and a portion of the sheet are bright can be imaged.

(3) The microneedle array imaging device according to (1) or (2), in which the imaging section images the microneedle array under conditions in which a direction in which the microneedle array is imaged becomes parallel to a direction in which the surface is irradiated with the illumination light.

According to the present aspect, the microneedle array is imaged along the direction in which the microneedle array is irradiated with the illumination light. In this manner, an image with a higher contrast can be imaged. In this case, the microneedle array is coaxially imaged. Here, the term "parallel" includes a state of almost being parallel.

(4) The microneedle array imaging device according to any one of (1) to (3), in which the illumination unit comprises: a light source unit which emits parallel light from a side of the surface on which the microneedles are arranged toward the microneedle array; and a reflection member which reflects the light transmitted through the microneedle array and irradiates the surface on the side opposite to the surface on which the microneedles are arranged with the illumination light.

According to the present aspect, the parallel light is emitted toward the microneedle array from the light source unit provided on the side of the surface on which the microneedles are arranged. Further, the light transmitted through the microneedle array is reflected on the reflection member and radiated to the surface on a side opposite to the surface on which the microneedles are arranged.

(5) A microneedle array imaging device comprising: an illumination unit which irradiates a surface on a side opposite to a surface on which a plurality of microneedles whose inclination angle of a side surface with respect to a bottom surface is θ° are arranged on a sheet to form a microneedle array, with illumination light; and an imaging section which images the microneedle array from a side of the surface on which the microneedles are arranged, in which, in a case where the microneedle arranged closest to an emission surface of the illumination light is set as a reference microneedle, the illumination unit irradiates the surface with the illumination light under conditions in which the intensity of light incident on the bottom surface of the reference microneedle at an incident angle of less than 90−θ° is 1/10 or less of the entire intensity of the light incident on the bottom surface of the reference microneedle and the intensity of light incident on the side surface of the reference microneedle at an incident angle greater than or equal to a critical angle is 1/10 or less of the entire intensity of the light incident on the bottom surface of the reference microneedle.

According to the present aspect, the surface on a side opposite to the surface on which the microneedles forming the microneedle array are arranged is irradiated with illumination light. In addition, the microneedle array is imaged from a side of the surface on which the microneedles are arranged. The surface is irradiated with the illumination light such that certain conditions are satisfied using the microneedle (reference microneedle) arranged closest to the emission surface as a reference. In other words, the surface is irradiated with the illumination light under conditions in which the intensity of light incident on the bottom surface of the reference microneedle at an incident angle of less than 90−θ° is 1/10 or less of the entire intensity of the light incident on the bottom surface of the reference microneedle and the intensity of light incident on the side surface of the reference microneedle at an incident angle greater than or equal to a critical angle is 1/10 or less of the entire intensity of the light incident on the bottom surface of the reference microneedle. In this manner, a state in which only the tip portion of the microneedle is dark and other portions, in other words, the base portion of the microneedle and the portion of the sheet are bright can be generated. Therefore, an image in which the shape and the like of the microneedle array are easily inspected can be obtained.

Further, the first condition, that is, the condition in which the intensity of light incident on the bottom surface of the reference microneedle at an incident angle of less than 90−θ° is 1/10 or less of the entire intensity of the light incident on the bottom surface of the reference microneedle is a condition derived from the inclination angle of the side surface of the microneedle. The light incident on the bottom surface of the microneedle at an incident angle of less than 90−θ° is propagated to the tip of the microneedle. However, in a case where light other than parallel light, such as diffused light, is used as the illumination light, the light to be incident under the above-described conditions cannot be completely eliminated. Therefore, the condition in which the intensity of light incident on the bottom surface of the reference microneedle at an incident angle of less than 90−θ° is set to be less than or equal to a certain value is defined as a requirement. In other words, the condition in which the intensity thereof is set to 1/10 or less of the entire intensity thereof is required. By setting the intensity of light to be incident under the above-described conditions to 1/10 or less of the entire intensity thereof, a state in which the tip of the microneedle is sufficiently dark can be generated, and an image with a contrast required for the inspection can be obtained. Further, the expression "the intensity thereof is 1/10 or less of the entire intensity thereof" means that, in a case where the entire intensity of light emitted from the emission surface and incident on the bottom surface of the reference microneedle is set to 1, the intensity thereof is 1/10 or less of the set entire intensity.

The second condition, that is, the condition in which the intensity of light incident on the side surface of the reference microneedle at an incident angle greater than or equal to a critical angle is 1/10 or less of the entire intensity of the light incident on the bottom surface of the reference microneedle is a condition derived from the viewpoint of the total reflection occurring inside the microneedle. In a case where the light incident on the microneedle is totally reflected inside the microneedle, the light is easily propagated to the tip of the microneedle. However, in a case where light other than parallel light, such as diffused light, is used as the illumination light, the total reflection cannot be completely eliminated. Therefore, the condition in which the intensity of light incident on the side surface of the reference microneedle at an incident angle greater than or equal to a critical angle is set to be less than or equal to a certain value of the entire intensity of the light incident on the bottom surface of the reference microneedle is defined as a requirement. In other words, the condition in which the intensity thereof is set to 1/10 or less of the entire intensity thereof is required. By setting the intensity of light to be incident under the above-described conditions to 1/10 or less of the entire intensity thereof, a state in which the tip of the microneedle is sufficiently dark can be generated, and an image with a contrast required for the inspection can be obtained. Further, the expression "the intensity thereof is 1/10 or less of the entire intensity thereof" means that, in a case where the entire intensity of light emitted from the emission surface and incident on the bottom surface of the reference microneedle is set to 1, the intensity thereof is 1/10 or less of the set entire intensity.

Both conditions are conditions for making light difficult to enter the tip of the microneedle. By irradiating the surface with illumination light such that two conditions described above are satisfied, an image in which only the tip portion of the microneedle is dark and other portions, in other words, the base portion of the microneedle and the portion of the sheet are bright can be imaged even in a case where light other than parallel light is used as the illumination light. In this manner, the microneedle array can be inspected with high accuracy based on the captured image.

Further, the reason why the microneedle arranged closest to the emission surface is used as a reference is because light is likely to be propagated to the tip portion of a microneedle as the microneedle is positioned closer to the emission surface. In other words, by using the tip portion of the microneedle arranged closest to the emission surface as a reference and setting the illumination light such that the tip portion of the microneedle to be dark, the tip portions of other microneedles can be necessarily darkened.

(6) The microneedle array imaging device according to (5), in which the illumination unit irradiates the surface with diffused light as illumination light.

According to the present aspect, diffused light is used as the illumination light. An image without unevenness as a whole can be obtained by using diffused light as the illumination light. In other words, a portion which is projected brightly can be made uniformly bright without unevenness by using diffused light as the illumination light. In this manner, an image suitable for the inspection can be obtained. Further, the illumination unit and the imaging section can also be easily set by using diffused light as the illumination light.

(7) The microneedle array imaging device according to (6), in which the emission surface is disposed perpendicularly to the sheet.

According to the present aspect, the emission surface is disposed perpendicularly to the sheet. In this manner, the condition in which light is unlikely to enter the tip of the microneedle can be prepared. Here, the term "perpendicular" includes a state of almost being perpendicular.

(8) The microneedle array imaging device according to (6) or (7), in which the imaging section images the microneedle array in a direction inclined with respect to the sheet.

According to the present aspect, the microneedle array is obliquely imaged. In this manner, an image in which the inspection and the like of the microneedle array can be obtained.

(9) The microneedle array imaging device according to any one of (6) to (8), in which the illumination unit comprises: a light source unit which emits light from a side of the surface on which the microneedles are arranged toward the microneedle array; and a diffusion reflection member which diffuses and reflects the light transmitted through the microneedle array and irradiates the surface on the side opposite to the surface on which the microneedles are arranged with the illumination light.

According to the present aspect, the light is emitted toward the microneedle array from the light source unit provided on a side of the surface where the microneedles are arranged. Further, the light transmitted through the microneedle array is diffused and reflected by the diffusion reflection member and radiated to the surface on a side opposite to the surface on which the microneedles are arranged. In this case, the surface that diffuses and reflects the light constitutes the emission surface in a diffusion plate.

(10) A microneedle array inspection device comprising: the microneedle array imaging device according to any one of (1) to (9); and an inspection unit which acquires an image captured by the microneedle array imaging device, and analyzes the obtained image to inspect the microneedle array.

According to the present aspect, the microneedle array is inspected based on the image captured by the microneedle array imaging device according to any one of (1) to (9). In this manner, the microneedle array can be inspected with high accuracy.

(11) A microneedle array imaging method comprising: irradiating a surface on a side opposite to a surface on which a plurality of microneedles whose inclination angle of a side surface with respect to a bottom surface is θ° are arranged on a sheet to form a microneedle array, with parallel light as illumination light; and imaging the microneedle array from a side of the surface on which the microneedles are arranged, in which the surface is irradiated with the illumination light under conditions in which an incident angle of light onto the bottom surface of the microneedle is 90−θ° or greater and an incident angle of light onto the side surface of the microneedle is less than a critical angle.

According to the present aspect, the surface on a side opposite to the surface on which the microneedles forming the microneedle array are arranged is irradiated with illumination light. In addition, the microneedle array is imaged from a side of the surface on which the microneedles are arranged. Parallel light is used as the illumination light and the surface is irradiated under certain conditions. In other words, the surface is irradiated with the illumination light under conditions in which an incident angle of light onto the bottom surface of the microneedle is 90−θ° or greater and an incident angle of light onto the side surface of the microneedle is less than a critical angle. In this manner, a state in which almost no light is emitted from a tip portion of the microneedle can be generated. As the result, an image in which only the tip portion of the microneedle is dark and other portions, in other words, the base portion of the microneedle and the portion of the sheet are bright can be imaged. Further, in this manner, the microneedle array can be inspected with high accuracy based on the obtained image. In other words, since an image with a high contrast can be obtained, the shape and the like of each microneedle can be inspected with high accuracy.

(12) A microneedle array imaging method comprising: irradiating a surface on a side opposite to a surface on which a plurality of microneedles whose inclination angle of a side surface with respect to a bottom surface is $\theta°$ are arranged on a sheet to form a microneedle array, with illumination light; and imaging the microneedle array from a side of the surface on which the microneedles are arranged, in which, in a case where the microneedle arranged closest to an emission surface of the illumination light is set as a reference microneedle, the surface is irradiated with the illumination light under conditions in which the intensity of light incident on the bottom surface of the reference microneedle at an incident angle of less than $90-\theta°$ is $\frac{1}{10}$ or less of the entire intensity of the light incident on the bottom surface of the reference microneedle and the intensity of light incident on the side surface of the reference microneedle at an incident angle greater than or equal to a critical angle is $\frac{1}{10}$ or less of the entire intensity of the light incident on the bottom surface of the reference microneedle.

According to the present aspect, the surface on a side opposite to the surface on which the microneedles forming the microneedle array are arranged is irradiated with illumination light. In addition, the microneedle array is imaged from a side of the surface on which the microneedles are arranged. The surface is irradiated with the illumination light such that certain conditions are satisfied using the microneedle (reference microneedle) arranged closest to the emission surface as a reference. In other words, the surface is irradiated with the illumination light under conditions in which the intensity of light incident on the bottom surface of the reference microneedle at an incident angle of less than $90-\theta°$ is $\frac{1}{10}$ or less of the entire intensity of the light incident on the bottom surface of the reference microneedle and the intensity of light incident on the side surface of the reference microneedle at an incident angle greater than or equal to a critical angle is $\frac{1}{10}$ or less of the entire intensity of the light incident on the bottom surface of the reference microneedle. In this manner, in the microneedle array, a state in which only the tip portion of the microneedle is dark and other portions are bright can be generated. Therefore, an image in which the shape and the like of the microneedle array are easily inspected can be obtained.

(13) A microneedle array inspection method comprising: acquiring an image captured using the microneedle array imaging method according to (11) or (12), and analyzing the obtained image to inspect the microneedle array.

According to the present aspect, the microneedle array is inspected based on the image captured by the microneedle array imaging method according to (11) or (12). In this manner, the microneedle array can be inspected with high accuracy.

According to the present invention, it is possible to inspect the microneedle array with high accuracy based on the obtained image.

DESCRIPTION OF THE PREFERRED EMBODIMENTS

Hereinafter, preferred embodiments of the present invention will be described in detail.

[Configuration of Microneedle Array]

First, the configuration of a microneedle array will be described.

<<Appearance Configuration>>

Figure 1:
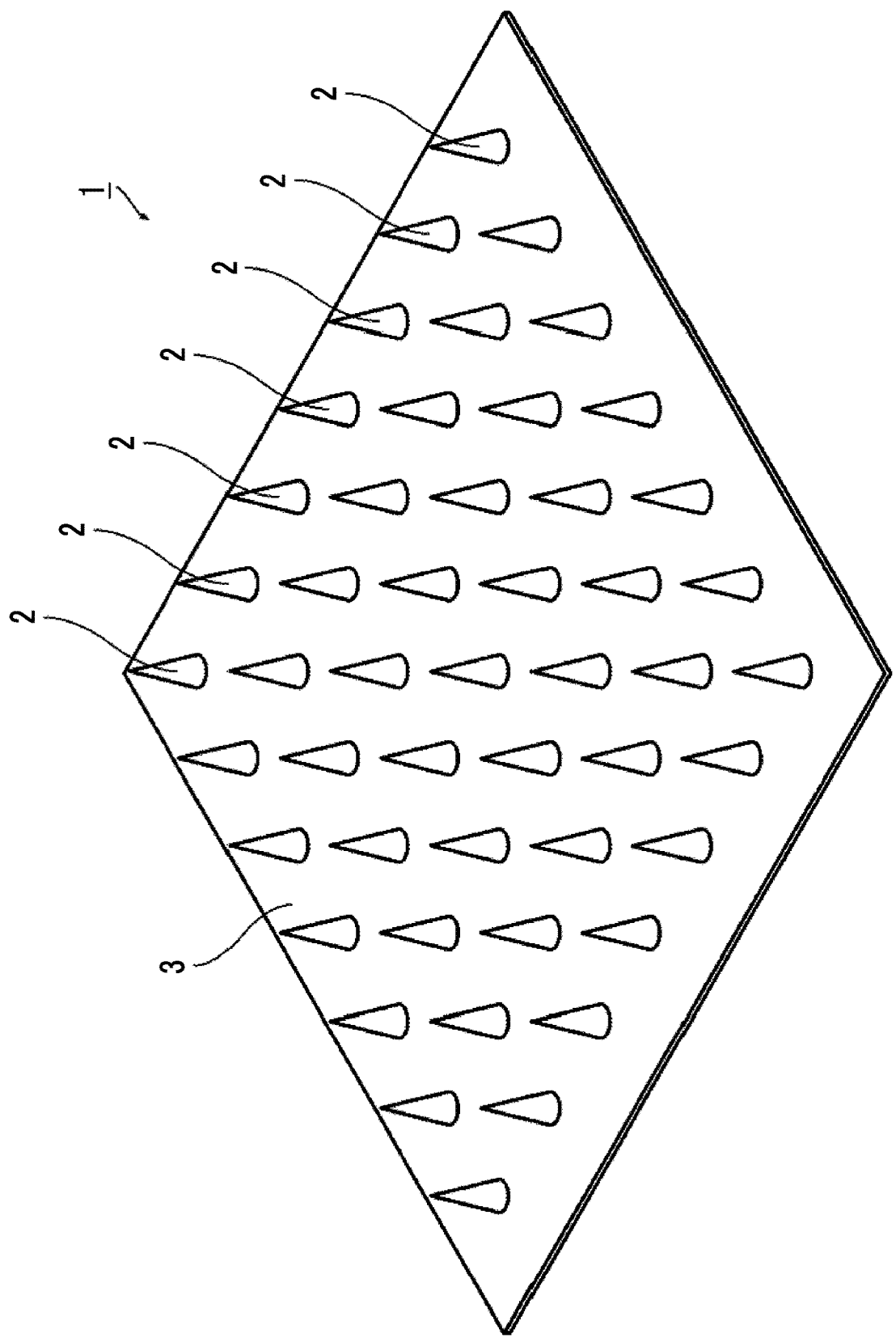
FIG. 1 is a perspective view illustrating an example of a microneedle array.

FIG. 1 is a perspective view illustrating an example of a microneedle array.

As illustrated in the same figure, a microneedle array 1 has a structure in which a plurality of microneedles 2 are regularly arranged on one surface of a sheet 3.

The microneedles 2 are portions punctured into the skin. The microneedles 2 have a needle shape. FIG. 1 illustrates an example in which the microneedles 2 have a conical shape. The microneedles 2 are regularly arranged on the sheet 3 at a constant density.

The arrangement interval of the microneedles 2 is not particularly limited, but it is preferable that the microneedles in one row are arranged at intervals of approximately 0.1 to 10 needles per 1 mm.

The density of the microneedles 2 is not particularly limited, but is preferably in a range of 10 to 5000 needles/$cm^2$, more preferably in a range of 25 to 1000 needles/$cm^2$, and still more preferably in a range of 25 to 400 needles/$cm^2$.

The height (length) of the microneedle 2 is expressed as the length of a perpendicular line drawn from the tip of the microneedle 2 to the sheet 3. The height of the microneedle 2 is not particularly limited, but is preferably in a range of 50 μm to 3000 μm, more preferably in a range of 100 μm to 1500 μm, and still more preferably in a range of 100 μm to 1000 μm.

An inclination angle ($\theta$) of the side surface of the microneedle 2 with respect to the bottom surface thereof is expressed as an angle between a cross section passing through the center of the microneedle 2 and the side surface. The inclination angle of the side surface of the microneedle 2 with respect to the bottom surface thereof is not particularly limited, but is preferably in a range of 70° to 85° and more preferably in a range of 77° to 78.5°.

The sheet 3 is a support of the microneedle 2. The sheet 3 has a planar shape. The microneedle 2 is comprised on one surface of the sheet 3. Hereinafter, the surface on which the microneedles 2 are provided is referred to as a first surface 3A and the surface on a side opposite to the first surface 3A is referred to as a second surface 3B so that both surfaces are distinguished from each other (see FIG. 2).

The area of the sheet 3 is not particularly limited, but is preferably in a range of 0.005 to 1000 mm$^2$, more preferably in a range of 0.05 to 500 mm$^2$, and still more preferably in a range of 0.1 to 400 mm$^2$.

The thickness of the sheet 3 is expressed as the distance between the first surface 3A and the second surface 3B of the sheet 3. The thickness of the sheet 3 is not particularly limited, but is preferably in a range of 1 μm to 2000 μm, more preferably in a range of 3 μm to 1500 μm, and still more preferably in a range of 5 μm to 1000 μm.

<<Composition>>

Figure 2:
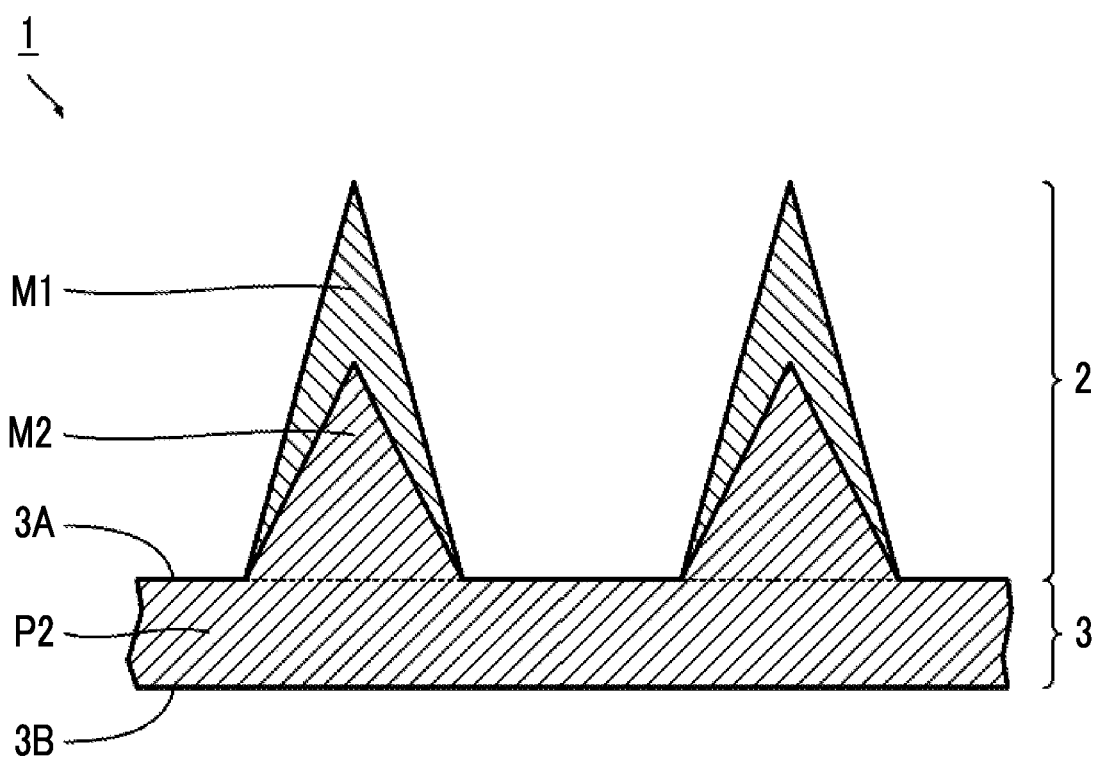
FIG. 2 is a cross sectional view illustrating some microneedles of the microneedle array.

FIG. 2 is a cross sectional view illustrating some microneedles of the microneedle array.

The microneedle 2 has a two-layer structure, and the tip portion and the base portion thereof are formed of materials different from each other. The tip portion thereof is formed of a material M1 that contains a drug, and the base portion is formed of a material M2 that does not contain a drug. The sheet 3 is formed of the material M2 that does not contain a drug, similarly to the base portion of the microneedle 2. The material M1 and the material M2 constituting the microneedle array 1 are transparent or semitransparent. Therefore, the microneedle array 1 is transparent or semitransparent as a whole.

The material M1 (material containing a drug) constituting the tip portion of the microneedle 2 is formed of, for example, a water-soluble polymer and a drug.

Examples of the water-soluble polymer contained in the material M1 include polysaccharides (such as hyaluronic acid, sodium hyaluronate, pullulan, dextran, dextrin, chondroitin sulfate, sodium chondroitin sulfate, carboxymethyl cellulose, hydroxypropyl cellulose, hydroxyethyl starch, polyvinylpyrrolidone, polyoxyethylene polyoxypropylene glycol, polyethylene glycol, and gum Arabic); proteins (such as gelatin); and biodegradable polymers (such as polylactic acid and a copolymer of lactic acid and glycolic acid). These may be used alone or in the form of a mixture of two or more kinds thereof.

Among the examples, as the water-soluble polymer contained in the material M1, polysaccharides are preferable, and hydroxyethyl starch, dextran, polyoxyethylene polyoxypropylene glycol, and polyethylene glycol are particularly preferable.

It is preferable that the water-soluble polymer contained in the material M1 does not interact with the drug contained in the material M1. For example, in a case where proteins are used as a drug and a charged polymer is mixed with the proteins, an associate is formed due to an electrostatic interaction between the proteins and the polymer, and the associate is aggregated and precipitated. Therefore, in a case where a charged material is used as a drug, it is preferable to use a water-soluble polymer that is not charged, such as hydroxyethyl starch, dextran, polyoxyethylene polyoxypropylene glycol, or polyethylene glycol.

The material M1 may contain at least one kind of saccharide selected from monosaccharides and disaccharides. Examples of the saccharide which can be contained in the material M1 constituting the tip portion of the microneedle 2 include monosaccharides such as glucose, fructose, erythrose, threose, ribose, lyxose, xylose, arabinose, allose, talose, gulose, altrose, mannose, idose, erythrulose, xylulose, ribulose, psicose, sorbose, tagatose, and galactose; and disaccharides such as sucrose, lactulose, lactose, maltose, trehalose, and cellobiose. Among these, sucrose is preferable.

A drug is a material having an effect on a human body.

It is preferable that the drug is selected from peptides or derivatives thereof, proteins, nucleic acid, polysaccharides, pharmaceutical compounds belonging to water-soluble low-molecular-weight compounds, and cosmetic ingredients.

The molecular weight of the drug is not particularly limited, but is preferably 500 or greater in a case of proteins.

Examples of peptides or derivatives thereof and proteins include calcitonin, adrenocorticotropic hormone, parathyroid hormone (PTH), hPTH (1→34), insulin, exendin, secretin, oxytocin, angiotensin, β-endorphin, glucagon, vasopressin, somatostatin, gastrin, luteinizing hormone releasing hormone, enkephalin, neurotensin, atrial natriuretic peptide, growth hormone, growth hormone releasing hormone, bradykinin, substance P, dynorphin, thyroid stimulating hormone, prolactin, interferon, interleukin, granulocyte colony stimulating factor (G-CSF), glutathione peroxidase, superoxide dismutase, desmopressin, somatomedin, endothelin, and salts of these.

Examples of the vaccines include influenza antigen, hepatitis B virus surface antigen (HBs antigen), hepatitis Be antigen (HBe antigen), Bacille de calmette et Guerin (BCG) antigen, measles antigen, rubella antigen, varicella antigen, yellow fever antigen, shingles antigen, rotavirus antigen, influenza bacilli b type (Hib) antigen, rabies antigen, cholera antigen, diphtheria antigen, pertussis antigen, tetanus antigen, inactivated polio antigen, Japanese encephalitis antigen, human papilloma antigen, and antigens obtained by mixing two to four types of these.

Among the examples, hormones or vaccines are preferable as the drug. As the hormones, growth hormones are particularly preferable.

The content of the drug is not particularly limited, but is preferably in a range of 0.01% to 50% by mass, more preferably in a range of 0.02% to 40% by mass, and still more preferably in a range of 0.02% to 30% by mass with respect to the mass of the water-soluble polymer contained in the material M1.

The material (material that does not contain a drug) M2 constituting the base portion of the microneedle 2 and the sheet 3 is formed of, for example, a water-soluble polymer.

Examples of the water-soluble polymer constituting the material M2 include polysaccharides (such as hyaluronic acid, sodium hyaluronate, pullulan, dextran, dextrin, chondroitin sulfate, sodium chondroitin sulfate, carboxymethyl cellulose, hydroxypropyl cellulose, hydroxyethyl starch, polyvinylpyrrolidone, polyoxyethylene polyoxypropylene glycol, polyethylene glycol, and gum Arabic); proteins (such as gelatin); and biodegradable polymers (such as polylactic acid and a copolymer of lactic acid and glycolic acid). Among the examples, polysaccharides are preferable, and dextran, hydroxyethyl starch, and chondroitin sulfate are particularly preferable.

The water-soluble polymer constituting the material M2 may be the same as the water-soluble polymer contained in the material M1. Further, the material M2 may contain additives.

[Microneedle Array Imaging Device]

The configuration of the microneedle array imaging device that images the microneedle array will be described.

The microneedle array imaging device is configured as a device that captures an image for inspection. An image for inspection indicates an image for inspecting a microneedle array using the obtained image. The inspection includes confirmation of whether or not the microneedle array is produced in a prescribed shape, cracking or chipping occurs, and foreign matter is mixed. The inspection is performed by analyzing the obtained image.

<<Configuration of Device>>

Figure 3:
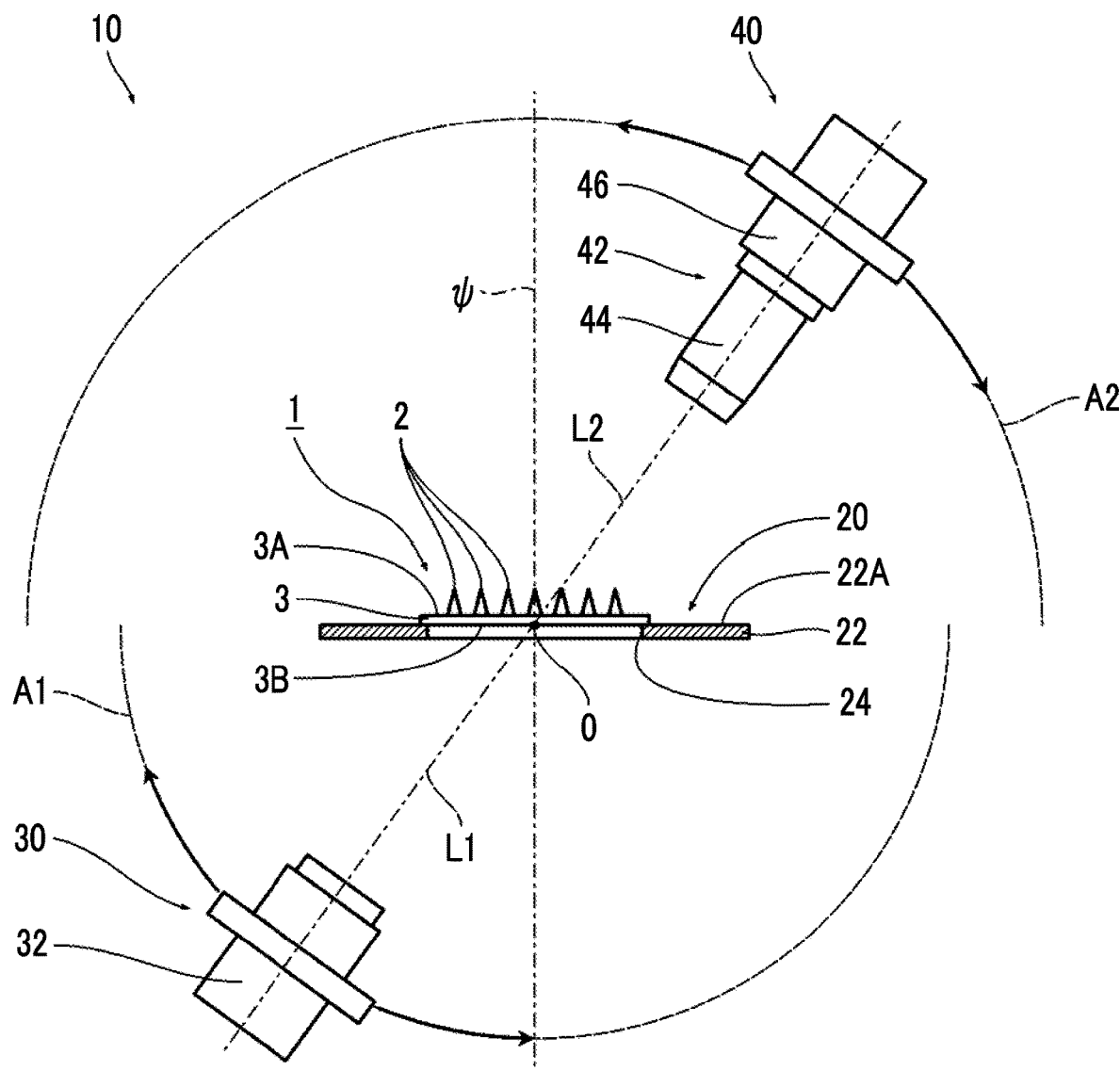
FIG. 3 is a schematic configuration view illustrating a microneedle array imaging device.

FIG. 3 is a schematic configuration view illustrating a microneedle array imaging device.

As illustrated in FIG. 3, a microneedle array imaging device 10 comprises a support portion 20 which supports the microneedle array 1; an illumination unit 30 which irradiates the second surface 3B of the sheet 3 of the microneedle array 1 supported by the support portion 20, with illumination light; and an imaging section 40 which images the microneedle array 1 supported by the support portion 20 from a side of the first surface 3A of the sheet 3.

<Support Portion>

The support portion 20 supports the microneedle array 1 to be inspected. The support portion 20 comprises a stage 22 that supports the microneedle array 1. The stage 22 comprises a horizontal placement surface 22A. The microneedle array 1 is placed on the placement surface 22A by allowing the second surface 3B of the sheet 3 to face downward. In this manner, the microneedle array 1 is horizontally supported. The stage 22 comprises an opening portion 24. The opening portion 24 is used as an illumination window for irradiating the microneedle array 1 placed on the stage 22 with illumination light. The microneedle array 1 is placed on the placement surface 22A such that a region where the microneedles 2 are arranged is positioned on the opening portion 24.

The support portion 20 comprises a rotary drive mechanism (not illustrated). The rotary drive mechanism passes through a center O of the placement surface 22A of the stage 22 and allows the stage 22 to horizontally rotate using an axis ψ orthogonal to the placement surface 22A as a rotation center.

<Illumination Unit>

The illumination unit 30 irradiates the second surface 3B of the sheet 3 where the microneedle array 1 supported by the support portion 20 is provided, with illumination light. The illumination unit 30 comprises a parallel light irradiation unit 32. The parallel light irradiation unit 32 comprises a light source and a lens (which are not illustrated) and emits parallel light. As the light source, for example, a white light emitting diode (LED) is used. The parallel light irradiation unit 32 emits parallel illumination light toward the stage 22. The parallel light irradiation unit 32 is set such that an optical axis L1 thereof passes through the center O of the placement surface 22A of the stage 22.

The illumination unit 30 further comprises an angle mechanism (not illustrated). The angle mechanism swingably supports the parallel light irradiation unit 32 in a constant angle range along an arc A1 using the center O of the placement surface 22A of the stage 22 as a center thereof. The irradiation direction of illumination light can be adjusted by adjusting the posture of the parallel light irradiation unit 32 of this angle mechanism. The setting of the irradiation direction will be described below.

<Imaging Section>

The imaging section 40 comprises an imaging unit 42. The imaging unit 42 comprises an imaging lens 44 and a camera 46. The camera 46 is a so-called digital camera, allows an imaging element to receive the light having passed through the imaging lens 44, converts the light into a digital signal, and outputs the signal. The imaging unit 42 is set such that an optical axis L2 of the imaging lens 44 passes through the center O of the placement surface 22A of the stage 22. Further, the imaging unit 42 and the parallel light irradiation unit 32 are disposed on the same plane. In other words, the optical axis L2 and the optical axis L1 of the parallel light irradiation unit 32 are disposed on the same plane.

The imaging section 40 further comprises an angle mechanism (not illustrated). The angle mechanism swingably supports the imaging unit 42 in a constant angle range along an arc A2 using the center O of the placement surface 22A of the stage 22 as a center thereof. The direction in which the microneedle array 1 on the stage 22 is imaged can be adjusted by adjusting the posture of the imaging unit 42 of this angle mechanism. The setting of the direction in which the microneedle array 1 is imaged will be described below.

<<Method of Imaging Microneedle Array>>

The illumination unit 30 irradiates the second surface 3B of the sheet 3 where the microneedle array 1 placed on the stage 22 is arranged with illumination light serving as parallel light, and the microneedle array 1 is imaged from a side of the first surface 3A of the sheet 3.

At this time, the microneedle array 1 is imaged by setting the illumination unit 30 and the imaging section 40 under the following conditions.

Figure 4:
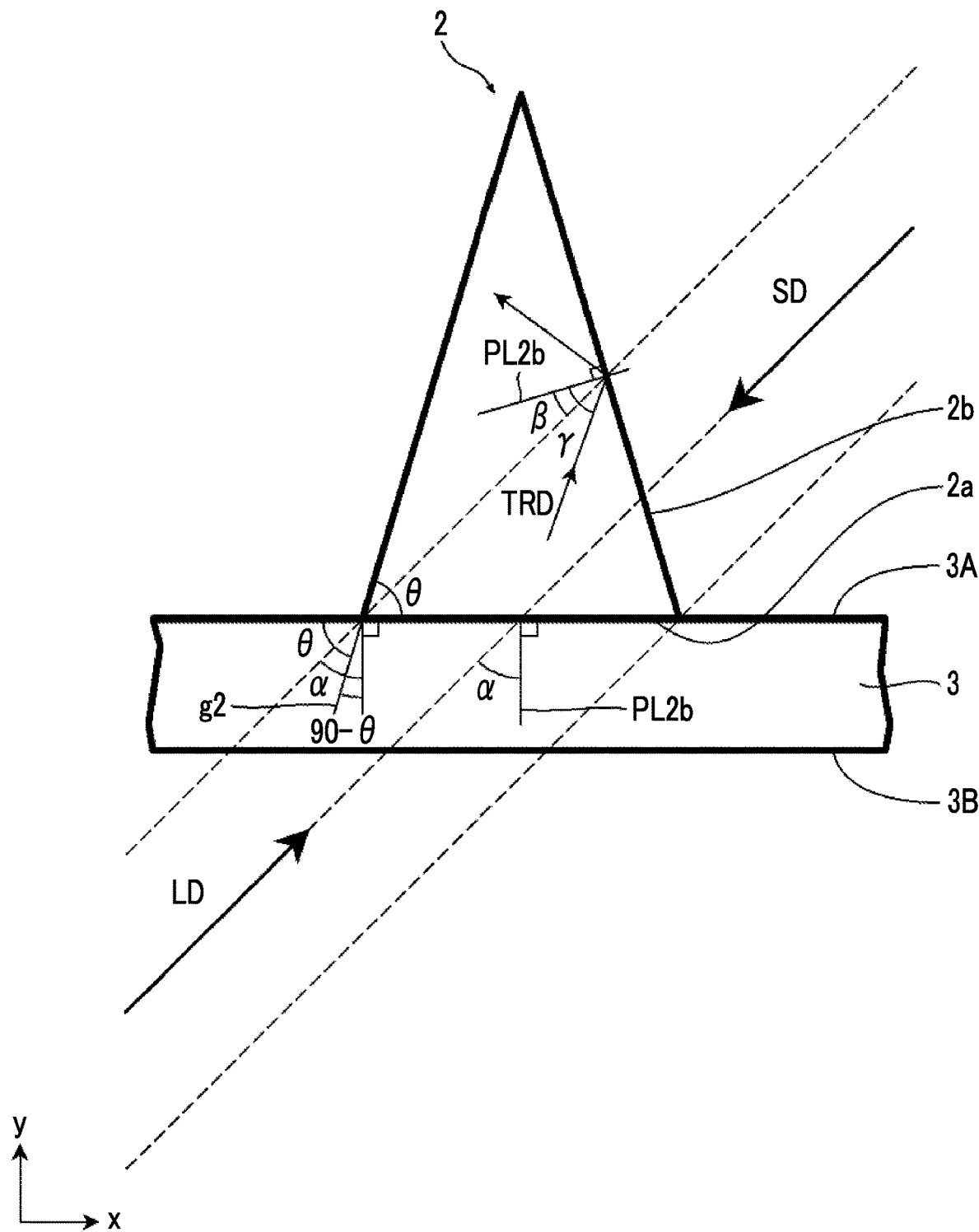
FIG. 4 is a conceptual view illustrating the setting of an illumination unit and an imaging section.

FIG. 4 is a conceptual view illustrating the setting of the illumination unit and the imaging section.

In the same figure, an arrow LD indicates the irradiation direction of illumination light radiated by the illumination unit 30, and an arrow SD indicates the imaging direction of the microneedle array 1 imaged by the imaging section 40. Further, the broken lines indicate the trajectories of the illumination light. Here, in order to simplify the description, refraction at the interface has not been considered.

<Setting of Illumination Unit>

The illumination unit 30 irradiates the surface with the illumination light under conditions in which an incident angle α of light onto a bottom surface $2a$ of the microneedle 2 is 90−θ° or greater and an incident angle β of light onto a side surface $2b$ of the microneedle 2 is less than a critical angle γ.

Here, the angle θ is an inclination angle of a side surface $2b$ with respect to a bottom surface $2a$ of the microneedle 2. This angle θ is defined as an angle between a conical bus bar constituting the microneedle 2 and the bottom surface $2a$ of the microneedle 2. Further, the bottom surface $2a$ of the microneedle 2 is defined as an interface between the microneedle 2 and the sheet 3.

The first condition, that is, the condition in which the incident angle α of light onto the bottom surface $2a$ of the microneedle 2 is 90−θ° or greater is a condition derived from the inclination angle θ of the side surface $2b$ of the microneedle 2.

The light incident on the bottom surface $2a$ of the microneedle 2 at an incident angle of less than 90−θ° is propagated to the tip of the microneedle 2.

Therefore, the condition in which the incident angle α of light on the bottom surface $2a$ of the microneedle 2 is 90−θ° or greater is defined as the first condition.

In this manner, propagation of light incident inside the microneedle 2 from the bottom surface $2a$ of the microneedle 2 to the tip thereof can be suppressed.

Further, the incident angle α of light onto the bottom surface $2a$ of the microneedle 2 is defined as an angle between the direction of light incident on the bottom surface 2a of the microneedle 2 and a normal line PL2a drawn on the bottom surface 2a of the microneedle 2.

Further, the angle 90−θ is defined as an angle between a straight line g2 formed by extending a conical bus bar constituting the microneedle 2 and the normal line PL2a drawn on the bottom surface 2a of the microneedle 2.

The second condition, that is, the condition in which the incident angle β of light onto the side surface 2b of the microneedle 2 is less than the critical angle γ is a condition for defining that the light incident on the microneedle 2 is not totally reflected inside.

In a case where the light incident inside the microneedle 2 from the bottom surface 2a of the microneedle 2 is totally reflected on the side surface 2b, the light is likely to be propagated to the tip of the microneedle 2.

Therefore, the condition in which light incident on the microneedle 2 is not totally reflected inside, in other words, the condition in which the incident angle β of light onto the side surface 2b of the microneedle 2 is less than the critical angle γ is defined as the second condition.

Here, the incident angle β of light incident on the side surface 2b of the microneedle 2 is defined as an angle between the direction of light incident on the side surface 2b of the microneedle 2 and a normal line PL2b drawn on the side surface 2b of the microneedle 2.

Further, the incident angle β of light onto the side surface 2b of the microneedle 2 indicates an incident angle of light, which enters the inside of the microneedle 2 from the bottom surface 2a of the microneedle 2, advances the inside of the microneedle 2, and is incident on the side surface 2b of the microneedle 2, onto the side surface 2b of the microneedle 2.

Further, the critical angle γ is defined as the smallest incident angle at which total reflection occurs. In FIG. 4, an arrow TRD indicates an incident direction of light that is totally reflected at the smallest incident angle on the side surface 2b of the microneedle 2. Therefore, the critical angle γ is defined as an angle between the direction of light indicated by the arrow TRD and the normal line PL2b drawn on the side surface 2b of the microneedle 2.

In a case of the microneedle array formed by mainly containing a water-soluble polymer, the critical angle γ is approximately 46°. Accordingly, in the case of the microneedle array formed by mainly containing a water-soluble polymer, the illumination light is radiated under conditions in which the incident angle of light onto the side surface 2b of the microneedle 2 is less than 46°.

Both of the first and second conditions described above are conditions for making light difficult to enter the tip of the microneedle 2. The irradiation direction of illumination light radiated by the illumination unit 30 is adjusted so as to satisfy two conditions described above. In this manner, a state in which only the tip portion of the microneedle 2 is dark and other portions, in other words, the base portion of the microneedle 2 and the portion of the sheet 3 are bright can be generated. Therefore, an image with a high contrast, in which the shape and the like of the microneedle array are easily inspected, can be obtained.

<Setting of Imaging Section>>

The imaging section 40 images the microneedle array 1 under conditions in which the direction in which the microneedle array 1 is imaged becomes parallel to the irradiation direction of illumination light. In other words, the microneedle array 1 is coaxially imaged. Here, the term "parallel" includes a state of almost being parallel (almost coaxial).

As described above, the illumination light is radiated under conditions in which the incident angle α of light onto the bottom surface 2a of the microneedle 2 is 90−θ° or greater. Therefore, the illumination light is obliquely radiated to the sheet 3. Accordingly, the microneedle array 1 is imaged obliquely with respect to the sheet 3.

As described above, by imaging the microneedle array 1 obliquely with respect to the sheet 3, the shape of the microneedle 2 can be easily inspected based on the obtained image.

Further, since the irradiation direction of the illumination light can be adjusted within the range satisfying the first and second conditions, the imaging direction is set as a preferable direction within the range where the illumination light can be adjusted.

Figure 5:
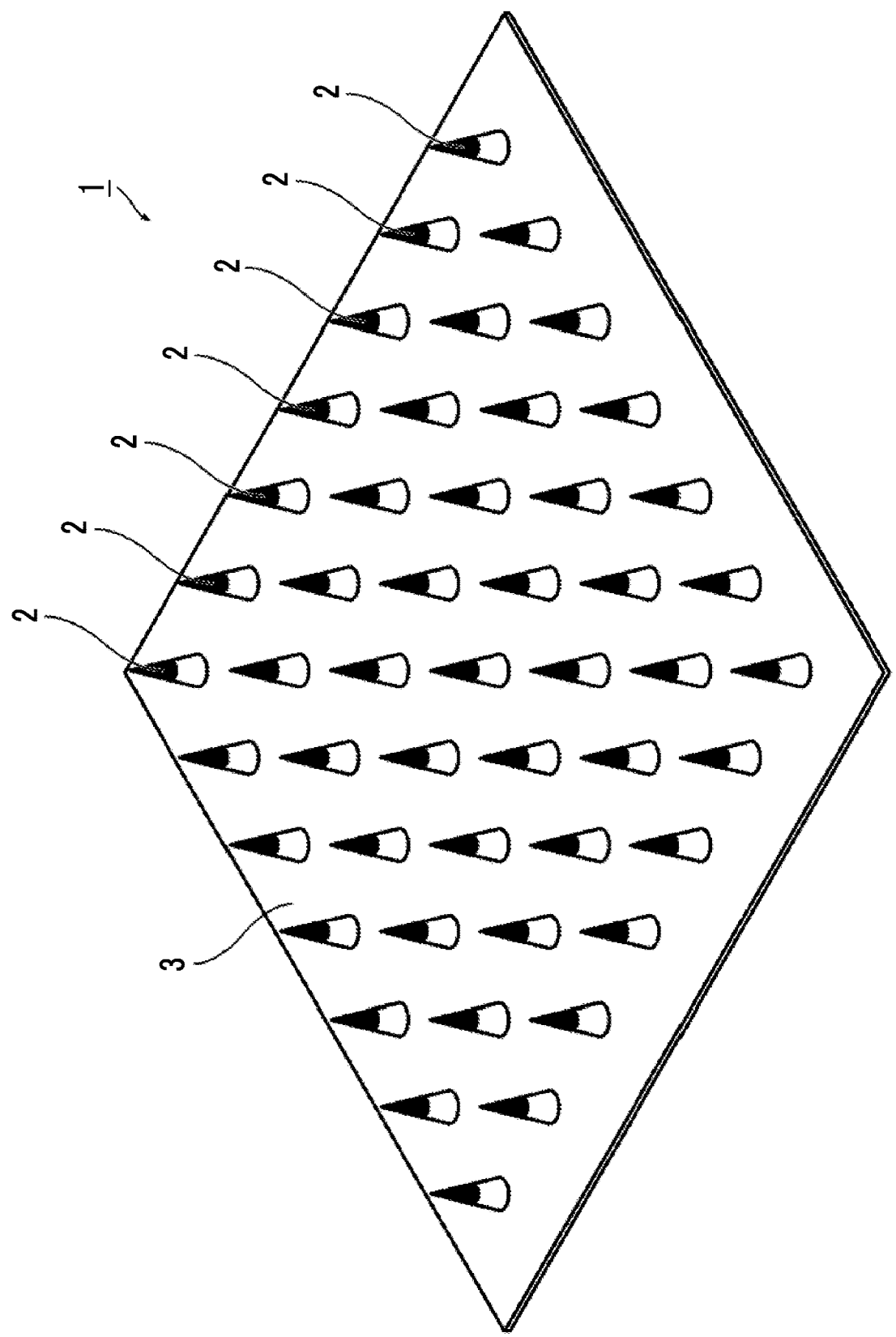
FIG. 5 is an image view illustrating an image obtained in a case where the illumination unit and the imaging section are appropriately set.

FIG. 5 is an image view illustrating an image obtained in a case where the illumination unit and the imaging section are appropriately set.

By appropriately setting the illumination unit 30 and the imaging section 40 and imaging the microneedle array 1, an image in which only the tip portion of the microneedle 2 is dark and other portions are bright can be obtained. In this manner, an image suitable for the inspection is obtained.

[Microneedle Array Inspection Device]

Next, a microneedle array inspection device 50 obtained by using the microneedle array imaging device 10 will be described.

<<Configuration of Microneedle Array Inspection Device>>

Figure 6:
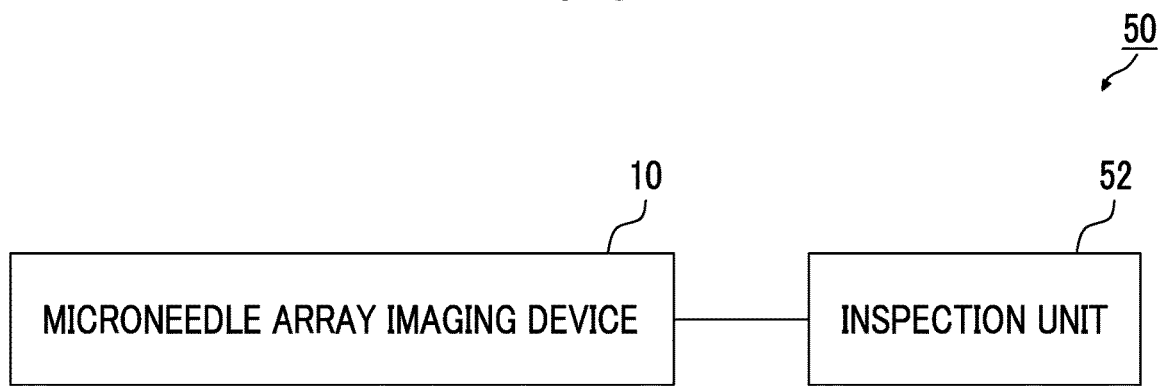
FIG. 6 is a block diagram showing the schematic configuration of a microneedle array inspection device.

FIG. 6 is a block diagram showing the schematic configuration of a microneedle array inspection device.

As shown in the same figure, the microneedle array inspection device comprises the microneedle array imaging device 10; and an inspection unit 52 which acquires image data of the microneedle array 1 imaged by the microneedle array imaging device 10 and inspects the microneedle array 1 based on the obtained image data.

The inspection unit 52 is connected so as to communicate with the microneedle array imaging device 10 in a wired or wireless manner and acquires image data of the microneedle array 1 imaged by the microneedle array imaging device 10. Moreover, the inspection unit 52 analyzes the obtained image data and performs inspection for predetermined items. For example, the inspection is performed to confirm whether or not each microneedle 2 is produced in a prescribed shape, cracking or chipping occurs in each microneedle 2, and foreign matter is mixed.

The inspection unit 52 is formed of a computer and the like. The computer functions as the inspection unit 52 by executing a predetermined inspection program. A display, an input device, a recording device, or the like is connected to the computer.

<<Microneedle Array Inspection Method>>

The method of inspecting the microneedle array 1 using the microneedle array inspection device 50 is as follows.

The microneedle array 1 to be inspected is imaged by the microneedle array imaging device 10.

The inspection unit 52 acquires image data of the imaged microneedle array 1 from the microneedle array imaging device 10. Further, the inspection unit 52 analyzes the obtained image data and performs inspection for predetermined items. At this time, an image with a high contrast is obtained, and thus the shape and the like of the microneedle array can be inspected with high accuracy.

Second Embodiment of Microneedle Array Imaging Device

<<Configuration of Device>>

Figure 7:
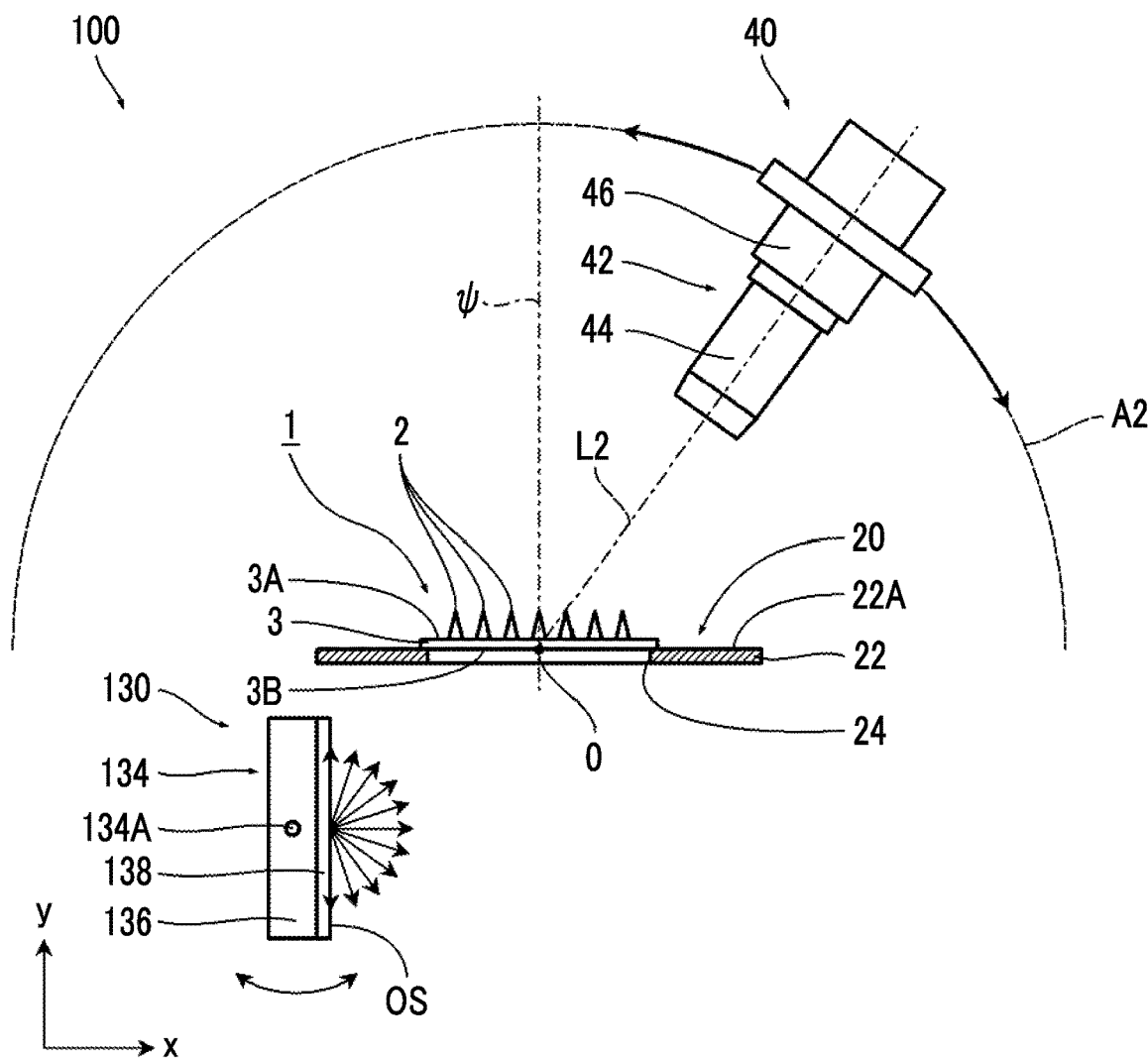
FIG. 7 is a schematic configuration view illustrating a second embodiment of a microneedle array imaging device.

FIG. 7 is a schematic configuration view illustrating a second embodiment of a microneedle array imaging device.

A microneedle array imaging device 100 according to the present embodiment is different from the microneedle array imaging device 10 according to the first embodiment in terms of the configuration of an illumination unit 130. The illumination unit 130 of the microneedle array imaging device 100 according to the present embodiment irradiates the second surface 3B of the sheet 3 where the microneedle array 1 placed on the stage 22 is arranged with light other than parallel light, as illumination light. Here, diffused light is radiated as the illumination light.

The configurations other than the configuration of the illumination unit 130 are the same as those of the microneedle array imaging device 10 according to the first embodiment. Therefore, only the configuration of the illumination unit 130 will be described here.

<Illumination Unit>

The illumination unit 130 comprises a diffused light irradiation unit 134 which emits diffused light. The diffused light irradiation unit 134 comprises a light source unit 136 and a diffusion plate 138.

The light source unit 136 comprises a light source (not illustrated) in a housing. As the light source, for example, a white LED is used.

The diffusion plate 138 is provided on a front surface of the light source unit 136 and allows the light emitted from the light source unit 136 to be diffused. The diffusion plate 138 is formed such that the surface on a side opposite to the light source unit 136 constitutes an emission surface OS of the diffused light. It is preferable that the diffusion plate 138 has diffusibility of complete diffusion or close to complete diffusion.

The illumination unit 130 further comprises a position adjustment mechanism (not illustrated) which adjusts a position where the diffused light irradiation unit 134 is installed, and an angle mechanism which adjusts the posture of the diffused light irradiation unit 134.

The position adjustment mechanism supports the diffused light irradiation unit 134 such that the position thereof can be adjusted in the front-back direction and the vertical direction. Here, the front-back direction is a direction in parallel with the placement surface 22A of the stage 22 in a horizontal state, in other words, a direction indicated by an arrow x in FIG. 7. Further, the vertical direction is a direction orthogonal to the placement surface 22A of the stage 22 in a horizontal state, in other words, a direction indicated by an arrow y in FIG. 7. The position of the emission surface OS can be adjusted by this position adjustment mechanism.

The angle mechanism swingably supports the diffused light irradiation unit 134 using a rocking shaft 134A provided in the diffused light irradiation unit 134 as the center. The rocking shaft 134A is orthogonal to the imaging direction of the imaging section 40. The inclination angle of the emission surface OS can be adjusted by this angle mechanism.

Further, FIG. 7 shows a case where the emission surface of the diffused light is set to be perpendicular to the sheet 3 of the microneedle array 1 placed on the stage 22.

<<Microneedle Array Imaging Method>>

The illumination unit 130 irradiates the second surface 3B of the sheet 3 where the microneedle array 1 placed on the stage 22 is arranged with illumination light which is diffused light, and the microneedle array 1 is imaged from the first surface 3A side of the sheet 3.

At this time, the microneedle array 1 is imaged by setting the illumination unit 130 and the imaging section 40 under the following conditions.

<Setting of Illumination Unit>

(1) Setting of Reference Microneedle

First, the reference microneedle is set. A reference microneedle 2x indicates a microneedle arranged closest to the emission surface OS.

Figure 8:
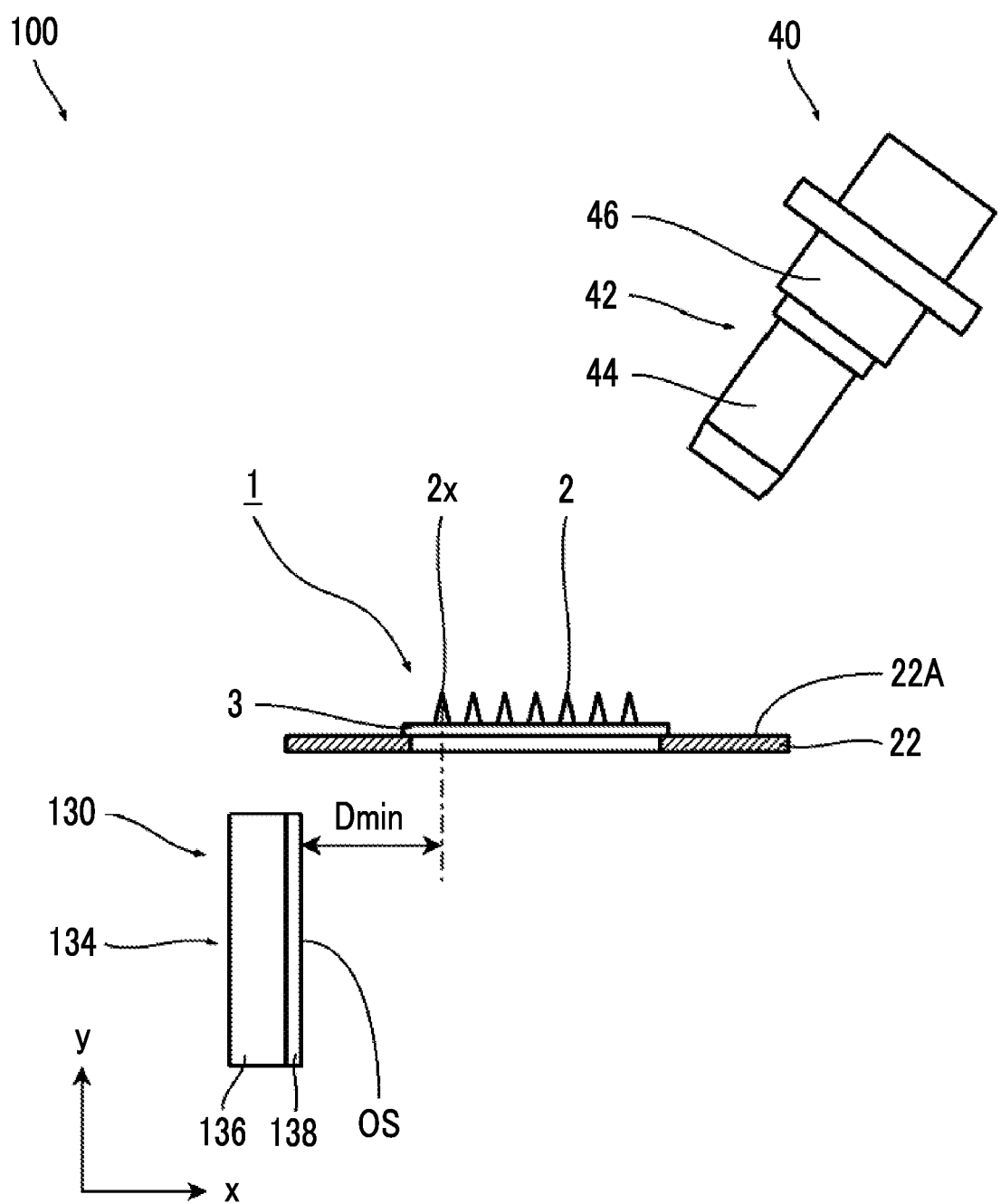
FIG. 8 is a conceptual view illustrating the setting of reference microneedles.

FIG. 8 is a conceptual view illustrating the setting of the reference microneedle.

As illustrated in the same figure, the microneedle arranged closest to the emission surface OS of diffused light is set as the reference microneedle 2x.

The reason why the microneedle arranged closest to the emission surface OS of diffused light is set as a reference is because light is likely to be propagated to the tip portion of a microneedle as the microneedle is positioned closer to the emission surface OS. In other words, the microneedle arranged closest to the emission surface OS is a microneedle in which light is most likely to be propagated to the tip portion thereof. Therefore, by using the tip portion of the microneedle arranged closest to the emission surface OS as a reference and setting the illumination light such that the tip portion of the microneedle to be dark, the tip portions of other microneedles can be necessarily darkened.

FIG. 8 illustrates an example in which the emission surface OS is provided perpendicularly to the sheet 3 of the microneedle array 1. In this case, a microneedle at a distance Dmin closest to the emission surface OS in a direction orthogonal to the emission surface OS is set as a reference microneedle 2x.

The entire intensity of light to be emitted from the emission surface OS of diffused light and to be incident on the bottom surface of the reference microneedle 2x is set to 1. The intensity of light here is the energy of light to be incident on the bottom surface of the reference microneedle 2x and can be considered as the illuminance.

(2) Setting of Illumination Unit

The illumination unit 130 radiates illumination light by setting, as the first condition, the emission surface OS such that the intensity of light incident on a bottom surface 2xa of the reference microneedle 2x at an incident angle of less than 90−θ° is $\frac{1}{10}$ or less of the entire intensity of light incident on the bottom surface 2xa of the reference microneedle 2x.

Further, the illumination unit 130 radiates illumination light by setting, as the second condition, the emission surface OS such that the intensity of light incident on a side surface 2xb of the reference microneedle 2x at an incident angle greater than or equal to the critical angle γ is $\frac{1}{10}$ or less of the entire intensity of light incident on the bottom surface 2xa of the reference microneedle 2x.

In this manner, in the microneedle array 1, a state in which only the tip portion of each microneedle 2 is dark and other portions, in other words, the base portion of the microneedle 2 and the portion of the sheet 3 are bright can be generated. Therefore, an image with a high contrast suitable for inspection on the shape and the like of the microneedle array can be obtained.

Hereinafter, each condition will be separately described.

(a) First Condition

The first condition, that is, the condition in which the intensity of light incident on the bottom surface 2xa of the reference microneedle 2x at an incident angle of less than 90−θ° is $\frac{1}{10}$ or less of the entire intensity of the light incident on the bottom surface 2xa of the reference microneedle 2x is a condition derived from the inclination angle θ of the side surface 2b of the microneedle 2. The light incident on the bottom surface 2a of the microneedle 2 at an incident angle of less than 90−θ° is propagated to the tip of the microneedle 2. However, in a case where diffused light is used as the illumination light, the light to be incident under the above-described conditions cannot be completely eliminated. Therefore, the condition in which the intensity of light incident on the bottom surface 2xa of the reference microneedle 2x at an incident angle of less than 90−θ° is set to be less than or equal to a certain value is defined as a requirement. In other words, the condition in which the intensity thereof is set to 1/10 or less of the entire intensity thereof is required. By setting the intensity of light to be incident under the above-described conditions to 1/10 or less of the entire intensity thereof, a state in which the tip of the microneedle is sufficiently dark can be generated, and an image with a contrast required for the inspection can be obtained.

Here, the expression "the intensity thereof is 1/10 or less of the entire intensity thereof" means that, in a case where the entire intensity of light emitted from the emission surface OS of diffused light and incident on the bottom surface 2xa of the reference microneedle 2x is set to 1, the intensity thereof is 1/10 or less of the set entire intensity. In other words, the expression means that, in the entire light incident on the bottom surface 2xa of the reference microneedle 2x, the intensity of light incident on the bottom surface 2xa of the reference microneedle 2x at an incident angle of less than 90−θ° is 1/10 of the entire intensity of light incident on the bottom surface 2xa of the reference microneedle 2x.

Figure 9:
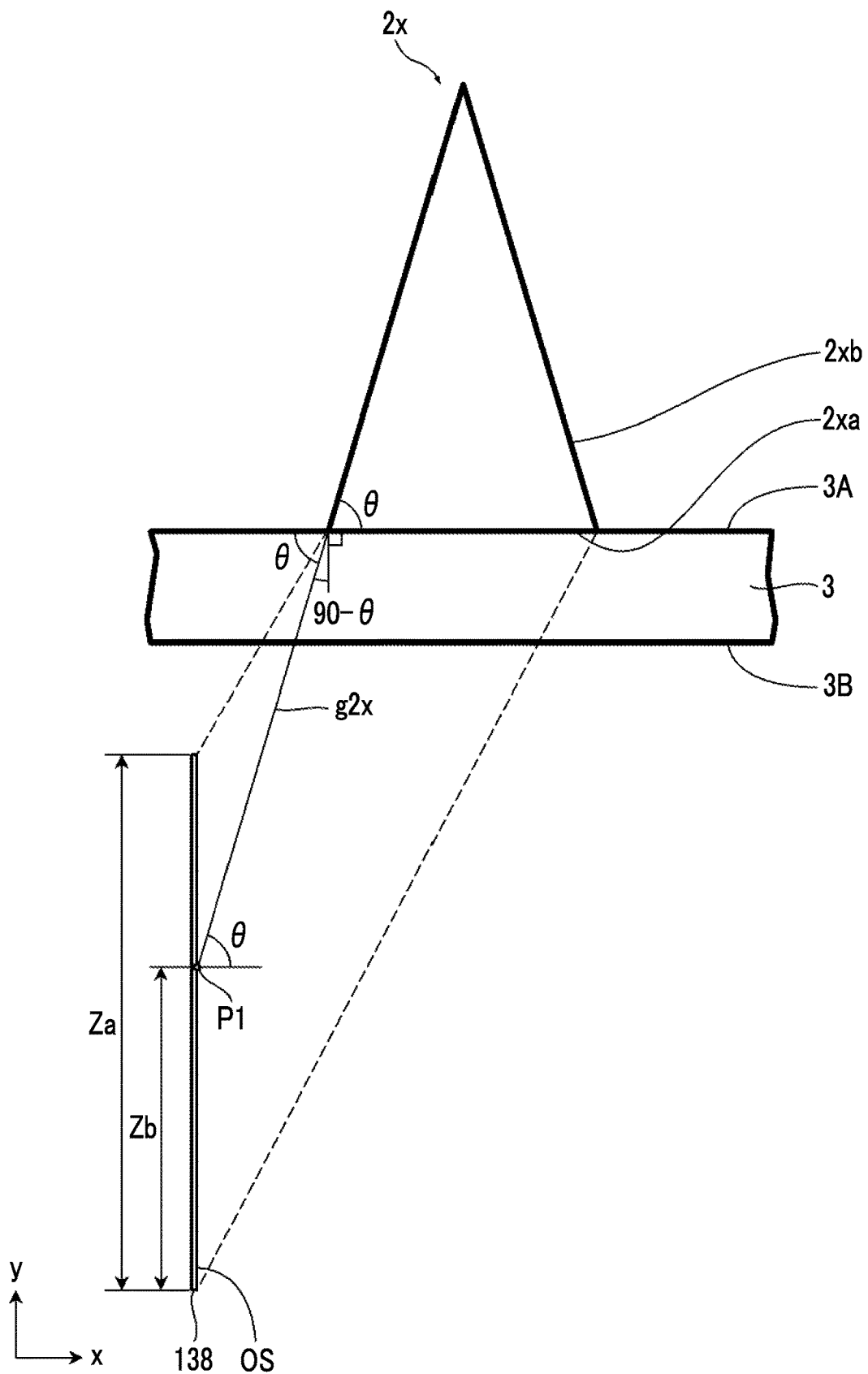
FIG. 9 is a view for describing light incident on a bottom surface of the reference microneedle at an incident angle of less than $90-\theta°$ in the entire light incident on the bottom surface of the reference microneedle.

FIG. 9 is a view for describing light incident on the bottom surface of the reference microneedle at an incident angle of less than 90−θ° in the entire light incident on the bottom surface of the reference microneedle.

Here, in order to simplify the description, the description will be made by limiting the incidence of light to incidence of light on a cross section orthogonal to the emission surface OS. Further, refraction at the interface has not been considered.

In a case where diffused light is emitted from the emission surface OS, light from the entire range Za of the emission surface OS is emitted to the bottom surface 2xa of the reference microneedle 2x. In FIG. 9, the light incident on the bottom surface 2xa of the reference microneedle 2x at an incident angle of less than 90−θ° is light to be emitted from a range Zb of the emission surface OS. This range Zb is defined as a range to a lower end of the emission surface OS from a point P1 which is an intersection between the emission surface OS and a straight line g2x obtained by extending a conical bus bar constituting the reference microneedle 2x.

The light to be emitted from a range on a side upper than the point P1 cannot enter the bottom surface 2xa at an incident angle of less than 90−θ° due to the positional relationship between the point P1 and the bottom surface 2xa.

Therefore, the emission surface OS may be set, as the first condition, such that the intensity of light emitted from the range Zb and incident on the bottom surface 2xa of the reference microneedle 2x is 1/10 of the intensity of light emitted from the entire range Za and incident on the bottom surface 2xa of the reference microneedle 2x.

(b) Second Condition

The second condition, that is, the condition in which the intensity of light incident on the side surface 2xb of the reference microneedle 2x at an incident angle greater than or equal to the critical angle γ is 1/10 or less of the entire intensity of the light incident on the bottom surface 2xa of the reference microneedle 2x is a condition derived from the viewpoint of the total reflection occurring inside the microneedle 2.

In a case where the light incident on the microneedle 2 is totally reflected inside the microneedle, the light is easily propagated to the tip of the microneedle 2. However, in a case where diffused light is used as the illumination light, the total reflection cannot be completely eliminated.

Therefore, the condition in which the intensity of light incident on the side surface 2xb of the reference microneedle 2x at an incident angle greater than or equal to the critical angle γ, that is, the intensity of light totally reflected inside the microneedle is set to be less than or equal to a certain value of the entire intensity of the light incident on the bottom surface 2xa of the reference microneedle 2x is defined as a requirement. In other words, the condition in which the intensity thereof is set to 1/10 or less of the entire intensity thereof is required. By setting the intensity of light to be incident under the above-described conditions to 1/10 or less of the entire intensity thereof, a state in which the tip of the microneedle is sufficiently dark can be generated, and an image with a contrast required for the inspection can be obtained.

Further, the expression "the intensity thereof is 1/10 or less of the entire intensity thereof" means that, in a case where the entire intensity of light emitted from the emission surface OS of diffused light and incident on the bottom surface 2xa of the reference microneedle 2x is set to 1, the intensity thereof is 1/10 or less of the set entire intensity. In other words, the expression means that, in the light incident on the bottom surface 2xa of the reference microneedle 2x, the intensity of light incident on the side surface 2xb of the reference microneedle 2x at an incident angle greater than or equal to the critical angle γ (the intensity of light incident on the bottom surface under conditions in which the light is totally reflected on the side surface) is 1/10 or less of the entire intensity of light emitted from the emission surface OS of diffused light and incident on the bottom surface 2xa of the reference microneedle 2x.

Figure 10:
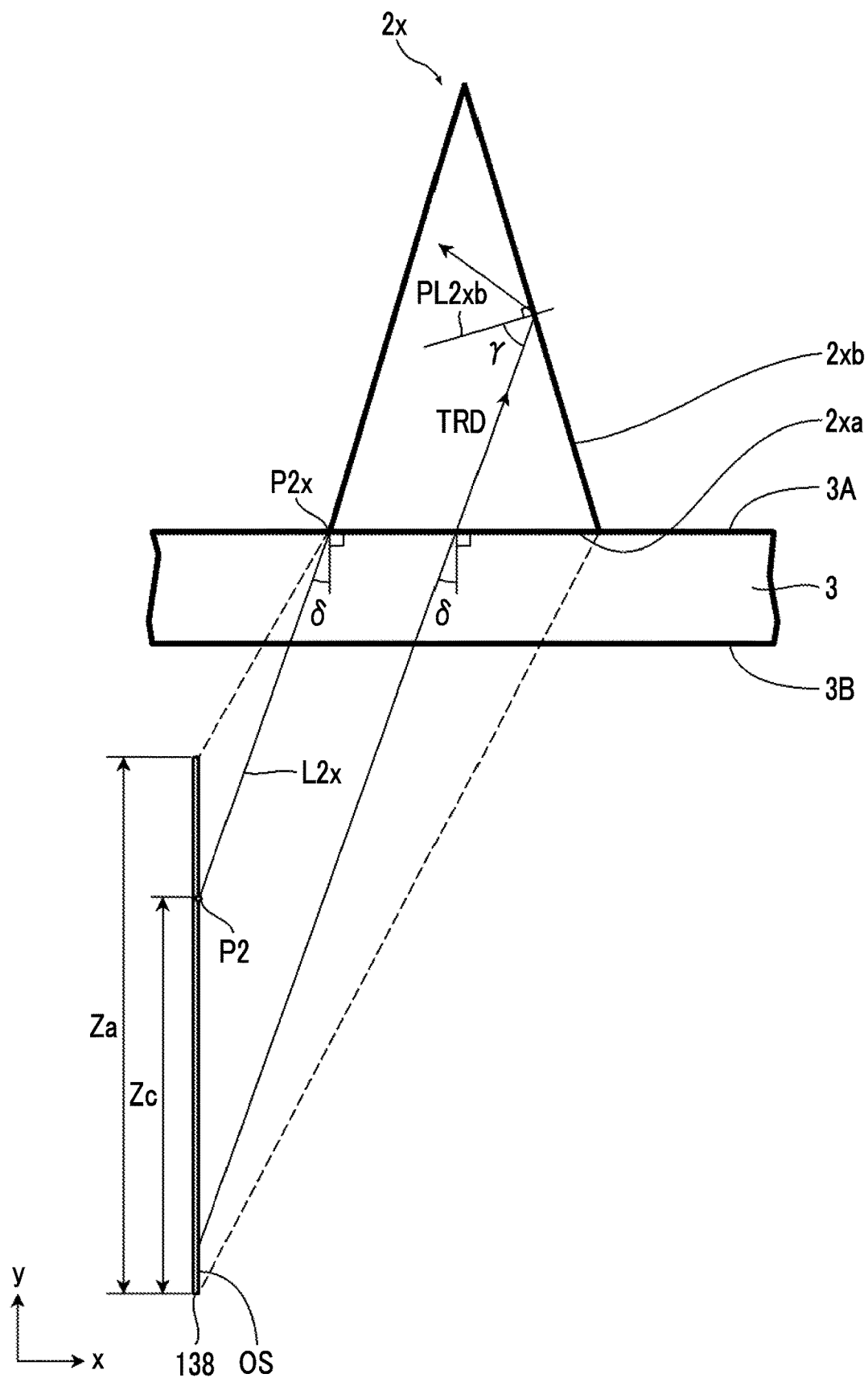
FIG. 10 is a view for describing light incident on a side surface of the reference microneedle at an incident angle greater than or equal to a critical angle in the entire light incident on the bottom surface of the reference microneedle.

FIG. 10 is a view for describing light incident on the side surface of the reference microneedle at an incident angle greater than or equal to a critical angle in the entire light incident on the bottom surface of the reference microneedle.

Here, in order to simplify the description, the description will be made by limiting the incidence of light to incidence of light on a cross section orthogonal to the emission surface OS. Further, refraction at the interface has not been considered.

In a case where diffused light is emitted from the emission surface OS, light from the entire range Za of the emission surface OS is emitted to the bottom surface 2xa of the reference microneedle 2x. In the entire light, the light incident on the side surface 2xb of the reference microneedle 2x at an incident angle greater than or equal to the critical angle γ is light to be emitted from a range Zc of the emission surface OS in FIG. 10. This range Zc is set in the following manner.

The incident angle at which light incident on the side surface 2xb of the reference microneedle 2x at the critical angle γ is incident on the bottom surface 2xa of the reference microneedle 2x is set as δ. The incident angle δ is defined as an angle between the incident direction TRD of light incident on the side surface 2xb of the reference microneedle 2x at the critical angle γ and a perpendicular line drawn from the bottom surface 2xa of the reference microneedle 2x.

The point closest to the emission surface OS is set as a point P2x on the bottom surface 2xa of the reference microneedle 2x. The ray trajectory of light incident on the point P2x at the incident angle δ is set as a straight line L2x. This range Zc is defined as a range to a lower end of the emission surface OS from a point P2 which is an intersection between the emission surface OS and the straight line L2x.

The light to be emitted from a range on a side upper than the point P2 cannot enter the bottom surface 2xa under a condition in which the light is totally reflected on the side surface 2xb due to the positional relationship between the point P2 and the bottom surface 2xa.

Therefore, the emission surface OS may be set, as the first condition, such that the intensity of light emitted from the range Zc and incident on the bottom surface 2xa of the reference microneedle 2x is 1/10 of the intensity of light emitted from the entire range Za and incident on the bottom surface 2xa of the reference microneedle 2x.

Both of the first and second conditions described above are conditions for making light difficult to enter the tip of the microneedle 2. The emission surface OS is set so as to satisfy two conditions described above. In this manner, a state in which only the tip portion of the microneedle 2 is dark and other portions, in other words, the base portion of the microneedle 2 and the portion of the sheet 3 are bright can be generated. Therefore, an image with a high contrast suitable for the inspection on the shape and the like of the microneedle array can be obtained.

<Setting of Imaging Section>

The imaging direction is set such that the imaging section 40 images the microneedle array 1 in a direction inclined with respect to the sheet 3. In other words, the imaging direction is set such that the microneedle array 1 is obliquely imaged. In this manner, an image in which the shape and the like of the microneedle array 1 are easily inspected can be obtained.

As described above, according to the microneedle array imaging device 10 of the present embodiment, an image in which only the tip portion of the microneedle 2 is dark and other portions are bright can be obtained. In this manner, an image with a high contrast suitable for the inspection is obtained.

Further, according to the microneedle array imaging device 10 of the present embodiment, an image without unevenness as a whole can be obtained by using diffused light as the illumination light. In other words, portions which are projected brightly (the base portion of each microneedle and the sheet portion) can be made uniformly bright without unevenness by using diffused light as the illumination light. In this manner, an image suitable for the inspection can be imaged.

Further, the illumination unit 30 and the imaging section 40 can be easily set by using diffused light as the illumination light. In other words, in a case where parallel light is used as the illumination light, the illumination unit 30 and the imaging section 40 are required to be set by being strictly adjusted. However, by using diffused light as the illumination light, the settable range can be made more flexible. As the result, the illumination unit 30 and the imaging section 40 can be easily set.

Further, it is preferable that the emission surface of diffused light is provided by being inclined with respect to the sheet 3 of the microneedle array 1 or provided perpendicularly to the sheet 3 thereof. This is because light easily enters the tip of the microneedle 2 in a case where the emission surface is provided parallel to the sheet 3 of the microneedle array 1 or at an angle close to being parallel. It is preferable that the emission angle of diffused light is provided by being inclined with respect to the sheet 3 at an inclination angle of 50° or greater and more preferable that the emission surface is provided perpendicularly to the sheet 3 of the microneedle array 1 or at an angle close to being perpendicular thereto.

Further, in a case where the emission surface of diffused light extremely approaches the second surface 3B of the sheet 3 of the microneedle array 1, light easily enters the tip of the microneedle 2. Accordingly, the emission surface of diffused light is separated from the second surface 3B of the sheet 3 of the microneedle array 1 preferably by a certain distance or longer and more preferably by a distance of 10 mm or greater.

Modification Example

In the embodiment described above, a case where diffused light and particularly light which is completely diffused are used as the illumination light has been described as an example, but a case where light diffused with directivity, light incident on the bottom surface of a microneedle at a plurality of incident angles, and the like are used as the illumination light can also be employed. In other words, in a case where light other than parallel light is used as the illumination light, a state in which only the tip portion of the microneedle 2 is dark and other portions are bright can be generated and an image with a high contrast suitable for the inspection on the shape and the like of the microneedle array can be obtained by setting the illumination unit and the imaging section under the above-described conditions.

Third Embodiment of Microneedle Array Imaging Device

<<Configuration of Device>>

Figure 11:
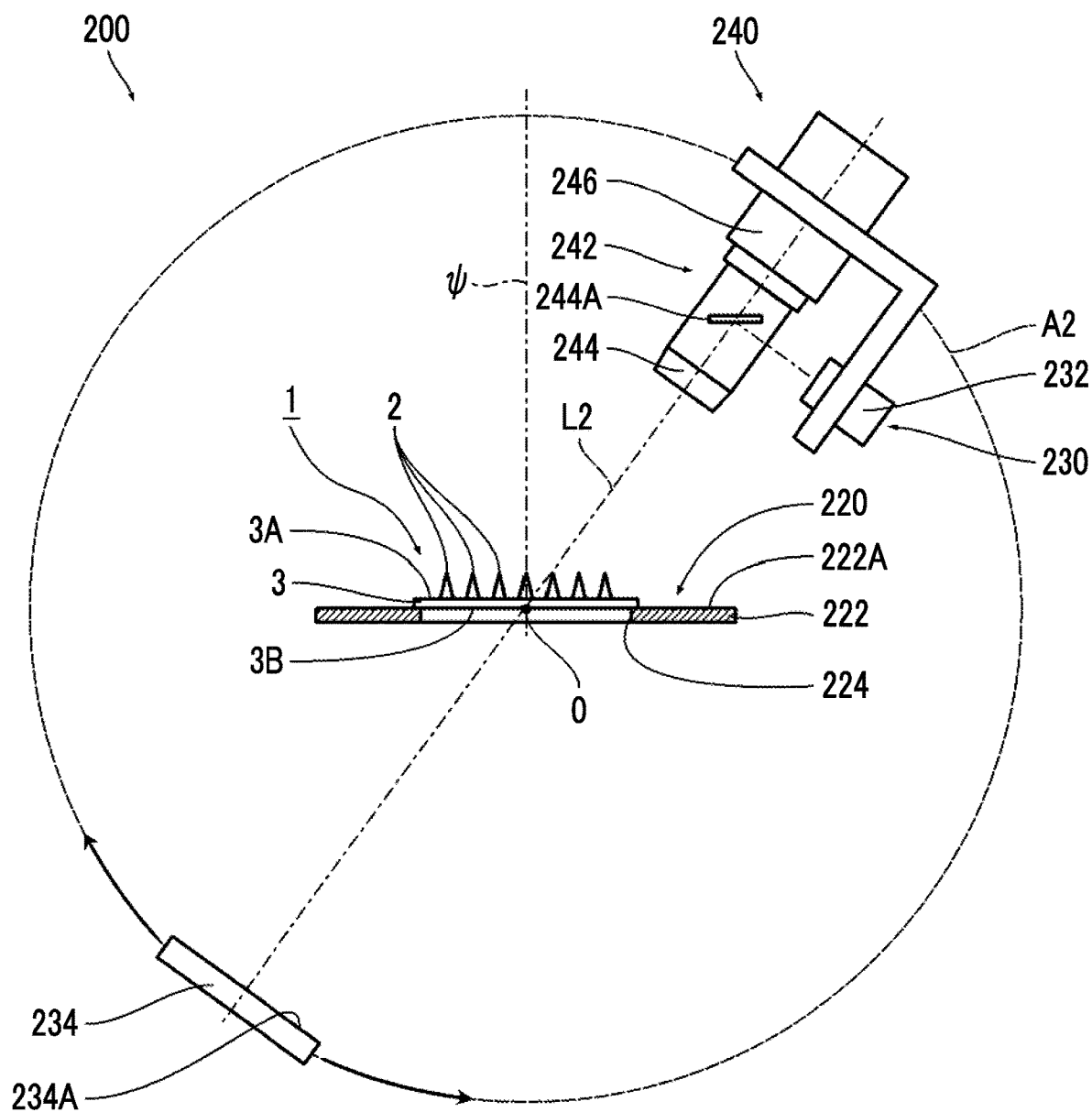
FIG. 11 is a schematic configuration view illustrating a third embodiment of a microneedle array imaging device.

FIG. 11 is a schematic configuration view illustrating a third embodiment of a microneedle array imaging device.

A microneedle array imaging device 200 according to the present embodiment is the same as the microneedle array imaging device 10 according to the first embodiment in terms of using parallel light as the illumination light.

Further, the microneedle array imaging device 100 according to the present embodiment is different from the microneedle array imaging device 10 according to the first embodiment in terms of irradiating the microneedle array 1 with illumination light from the first surface 3A side of the sheet 3.

The illumination light which is parallel light radiated to the microneedle array 1 from the first surface 3A side of the sheet 3 passes through the microneedle array 1 and is incident on a reflection surface 234A of a reflection plate 234 disposed on the second surface 3B side of the sheet 3. In addition, the illumination light is reflected on the reflection surface 234A and radiated to the second surface 3B of the sheet 3.

The microneedle array imaging device 200 according to the present embodiment comprises a support portion 220 which supports the microneedle array 1; an illumination unit 230 which irradiates the microneedle array 1 supported by the support portion 220 with illumination light; and an imaging section 240 which images the microneedle array 1 supported by the support portion 220.

[Support Portion]

The configuration of the support portion 220 is the same as the configuration of the support portion 20 of the microneedle array imaging device 10 according to the first embodiment. In other words, the support portion 220 comprises a stage 222 on which the microneedle array 1 is placed. The microneedle array 1 is placed on a placement surface 222A of the stage 222 by allowing the second surface 3B of the sheet 3 to face downward. The stage 222 comprises an opening portion 224. The illumination light radiated from the first surface 3A side of the sheet 3 is transmitted through the microneedle array 1, passes through the opening portion 224, and is incident on the reflection surface 234A of the reflection plate 234.

[Imaging Section]

The configuration of the imaging section 240 is the same as the configuration of the imaging section 40 of the microneedle array imaging device 10 according to the first embodiment. In other words, the imaging section 240 comprises an imaging unit 242 which images the microneedle array 1 placed on the placement surface 222A of the stage 222 from the first surface 3A side of the sheet 3. The imaging unit 242 comprises a lens 244 and a camera 246. Further, the lens 244 comprises a half mirror 244A on the optical path thereof in order to realize coaxial illumination.

The imaging section 240 further comprises an angle mechanism (not illustrated). The angle mechanism swingably supports the imaging unit 242 in a constant angle range along an arc A2 using the center O of the placement surface 222A of the stage 222 as a center thereof. The angle at which the microneedle array is imaged can be adjusted by adjusting the posture of the imaging unit 242 of this angle mechanism.

[Illumination Unit]

The illumination unit 230 comprises a parallel light irradiation unit 232 and the reflection plate 234. The parallel light irradiation unit 232 comprises a light source and a lens (not illustrated) and emits parallel light. The parallel light irradiation unit 232 emits illumination light which is parallel light toward the half mirror 244A provided on the lens 244 of the imaging unit 242. The travelling direction of the illumination light incident on the half mirror 244A is bent at a right angle, and the illumination light is propagated on the same optical axis as the lens 244 of the imaging unit 242. In this manner, the illumination light can be radiated coaxially with the camera 246 of the imaging unit 242. The parallel light irradiation unit 232 and the half mirror 244A constitute a light source unit.

The parallel light irradiation unit 232 is provided integrally with the imaging unit 242. Therefore, the imaging unit 242 is allowed to swing by the angle mechanism, the parallel light irradiation unit 232 also swings integrally with the imaging unit 242.

The reflection plate 234 is an example of a reflection member. The reflection plate 234 is formed of, for example, a mirror. The reflection plate 234 is disposed such that the reflection surface 234A faces the imaging unit 242 by interposing the stage 222 therebetween. In other words, the reflection plate 234 is disposed coaxially with the imaging unit 242, and the reflection surface 234A is disposed orthogonally to the optical axis L2 of the lens 244. The reflection surface 234A of the reflection plate 234 functions as an emission surface of illumination light radiated to the microneedle array 1.

The reflection plate 234 comprises an interlocking mechanism (not illustrated) and swings in conjunction with the imaging unit 242. In other words, in a case where the imaging unit 242 is allowed to swing, the reflection plate swings integrally with the imaging unit 242 so as to maintain the coaxial relationship.

<<Imaging Method>>

In a case where the parallel light irradiation unit 232 is driven, illumination light which is parallel light is incident on the half mirror 244A provided on the lens 244 of the imaging unit 242. The illumination light incident on the half mirror 244A is propagated on the same optical axis as the optical axis L2 of the lens 244 and is radiated to the first surface 3A of the sheet 3 of the microneedle array 1 on the stage 222. The illumination light radiated to the first surface 3A of the sheet 3 is transmitted through the sheet 3 and is incident on the reflection surface 234A of the reflection plate 234. Further, the illumination light is reflected on the reflection surface 234A and radiated to the second surface 3B of the sheet 3 of the microneedle array 1.

By adjusting the posture of the imaging unit 242 using the angle mechanism (not illustrated), the irradiation direction of illumination light is adjusted so that a state in which only the tip portion of the microneedle 2 is darkened is made. In other words, the irradiation direction of illumination light is adjusted such that the illumination light is radiated under conditions in which the incident angle of light onto the bottom surface of the microneedle 2 is 90−θ° or greater and the incident angle of light onto the side surface of the microneedle 2 is less than the critical angle.

In this manner, a state in which only the tip portion of the microneedle 2 is dark and other portions are bright can be generated and an image with a high contrast suitable for the inspection on the shape and the like of the microneedle array can be obtained.

Modification Example

<<Modification Example of Method of Radiating Illumination Light>>

A method of radiating illumination light in a coaxial direction with the camera 246 is not limited to the example described above. For example, a configuration in which illumination light is radiated in the coaxial direction with the camera 246 using ring illumination can be employed.

<Use of Polarizing Filter>

In a case where the microneedle array 1 is irradiated with illumination light from the first surface 3A side of the sheet 3, light which is specularly reflected is incident on the camera 246 and this may result in degradation of the contrast. In this case, the influence of the specular reflection light can be suppressed by using a polarizing filter. The light which is specularly reflected becomes polarized light having a vibration direction on the reflection surface. Therefore, a linear polarizing filter in a direction perpendicular to the reflection surface is inserted onto an imaging optical axis. In this manner, specular reflection light can be suppressed, and a clear image with a high contrast can be obtained.

Fourth Embodiment of Microneedle Array Imaging Device

<<Configuration of Device>>

Figure 12:
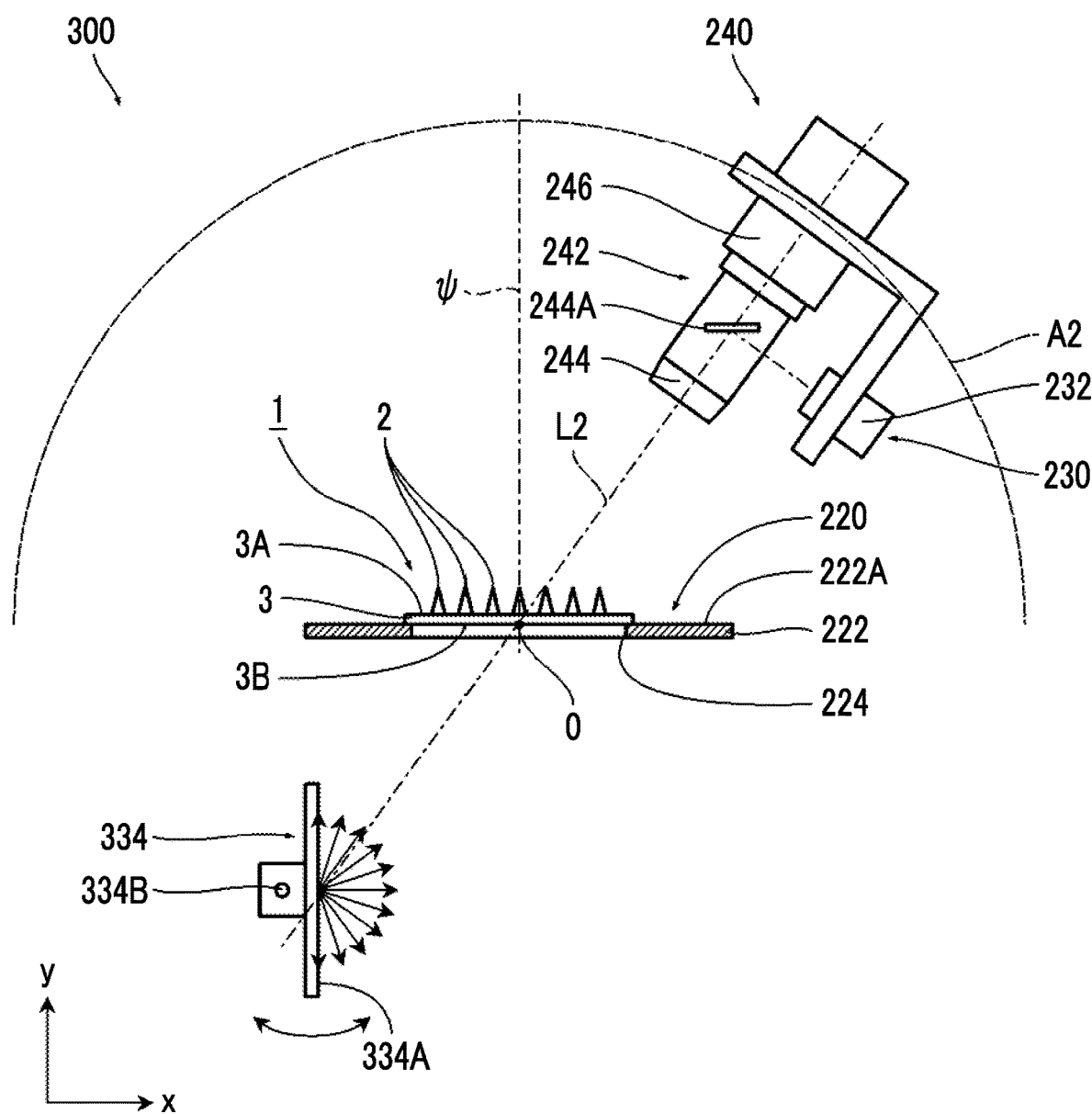
FIG. 12 is a schematic configuration view illustrating a fourth embodiment of a microneedle array imaging device.

FIG. 12 is a schematic configuration view illustrating a fourth embodiment of a microneedle array imaging device.

A microneedle array imaging device 300 according to the present embodiment is the same as the microneedle array imaging device 100 according to the second embodiment in terms of using diffused light as the illumination light.

Further, the microneedle array imaging device 300 according to the present embodiment is different from the microneedle array imaging device 100 according to the second embodiment in terms of irradiating the microneedle array 1 with illumination light from the first surface 3A side of the sheet 3.

The illumination light radiated to the microneedle array 1 from the first surface 3A side of the sheet 3 passes through the microneedle array 1 and is incident on a diffusion reflection surface 334A of a diffuse reflection plate 334 provided on the second surface 3B side of the sheet 3. In addition, the illumination light is diffused and reflected on the diffusion reflection surface 334A and radiated to the second surface 3B of the sheet 3.

The configurations other than the configuration of the illumination unit 330 are the same as those of the microneedle array imaging device 200 according to the third embodiment. Therefore, only the configuration of the illumination unit 330 will be described here.

[Illumination Unit]

The illumination unit 330 comprises an illumination light irradiation unit 332 and the diffuse reflection plate 334. The illumination light irradiation unit 332 comprises a light source and a lens (not illustrated) and emits illumination light. The illumination light is not limited to parallel light. The illumination light irradiation unit 332 emits illumination light toward the half mirror 244A provided on the lens 244 of the imaging unit 242. The travelling direction of the illumination light incident on the half mirror 244A is bent at a right angle, and the illumination light is propagated on the same optical axis as the lens 244 of the imaging unit 242. The illumination light irradiation unit 332 and the half mirror 244A constitute a light source unit.

The illumination light irradiation unit 332 is provided integrally with the imaging unit 242. Therefore, the imaging unit 242 is allowed to swing by the angle mechanism, the illumination light irradiation unit 332 also swings integrally with the imaging unit 242.

The diffuse reflection plate 334 is an example of a diffusion reflection member. It is preferable that the diffuse reflection plate 334 has diffusibility of complete diffusion or close to complete diffusion. The diffusion reflection surface 334A of the diffuse reflection plate 334 constitutes an irradiation surface of illumination light radiated to the microneedle array 1.

The illumination unit 330 further comprises a position adjustment mechanism (not illustrated) which adjusts a position where the diffuse reflection plate 334 is installed, and an angle mechanism which adjusts the posture of the diffuse reflection plate 334.

The position adjustment mechanism supports the diffuse reflection plate 334 such that the position thereof can be adjusted in the front-back direction and the vertical direction. Here, the front-back direction is a direction in parallel with the placement surface 222A of the stage 222 in a horizontal state, in other words, a direction indicated by an arrow x in FIG. 12. Further, the vertical direction is a direction orthogonal to the placement surface 222A of the stage 222 in a horizontal state, in other words, a direction indicated by an arrow y in FIG. 12. The position of the diffusion reflection surface 334A which is the emission surface can be adjusted by this position adjustment mechanism.

The angle mechanism swingably supports the diffuse reflection plate 334 using a rocking shaft 334B provided on the rear surface of the diffuse reflection plate 334 as the center. The rocking shaft 334B is orthogonal to the imaging direction of the imaging section 240. The inclination angle of the diffusion reflection surface 334A which is an emission surface can be adjusted by this angle mechanism.

<<Imaging Method>>

In a case where the illumination light irradiation unit 332 is driven, illumination light is incident on the half mirror 244A provided on the lens 244 of the imaging unit 242. The illumination light incident on the half mirror 244A is propagated in the optical axis direction of the lens 244 and is radiated to the first surface 3A of the sheet 3 of the microneedle array 1 on the stage 222. The illumination light radiated to the first surface 3A of the sheet 3 is transmitted through the sheet 3 and is incident on the reflection surface 334A of the diffuse reflection plate 334. Further, the illumination light is diffused and reflected on the diffusion reflection surface 334A and radiated to the second surface 3B of the sheet 3 of the microneedle array 1.

By adjusting the posture of the diffuse reflection plate 334 using the position adjustment mechanism and the angle mechanism (not illustrated), the irradiation direction of illumination light radiated to the microneedle array 1 is adjusted so that a state in which only the tip portion of the microneedle 2 is darkened is made. In other words, the position and the posture of the diffuse reflection plate 334 are adjusted such that the intensity of light incident on the bottom surface $2xa$ of the reference microneedle $2x$ at an incident angle of less than 90−θ° is 1/10 or less of the entire intensity of light incident on the bottom surface $2xa$ of the reference microneedle $2x$ and the intensity of light incident on the side surface $2xb$ of the reference microneedle $2x$ at an incident angle greater than or equal to the critical angle γ is 1/10 or less of the entire intensity of light incident on the bottom surface $2xa$ of the reference microneedle $2x$.

Further, the imaging direction is adjusted by adjusting the position of the imaging unit 242 using the angle mechanism. At this time, the imaging direction is set such that the microneedle array 1 is obliquely imaged.

In this manner, an image in which only the tip portion of the microneedle 2 is dark and other portions are projected brightly can be obtained.

Modification Example

The method of radiating illumination light in the coaxial direction with the camera 246 is not limited to the example described above. For example, a configuration in which illumination light is radiated in the coaxial direction with the camera 246 using ring illumination can be employed. Moreover, the influence of the specular reflection light can be suppressed by using a polarizing filter.

Other Embodiments

An optical system of an imaging section may be formed of a telecentric optical system. In this manner, an image can be captured without changing the size of the image even in a case where the focal point is shifted. Further, an image without distortion caused by the parallax can be captured.

Other Examples of Microneedle Arrays

The microneedle array which is the object of the present invention is not limited to the configurations described in the embodiments above. The present invention can be applied in a case of a microneedle array formed by a plurality of transparent or semitransparent microneedles being arranged on a transparent or semitransparent sheet.

The shape of the microneedles in the microneedle array is not particularly limited. In the example described above, the microneedles have a conical shape, but the present invention can also be similarly applied to a microneedle array comprising microneedles having a pyramid shape such as a quadrangular pyramid or a trigonal pyramid.

Further, the present invention can also be similarly applied to a microneedle array in which the microneedles have a multistage structure. A microneedle having a multistage structure indicates a microneedle having a structure in which the diameter thereof gradually decreases toward the tip thereof.

Figure 13:
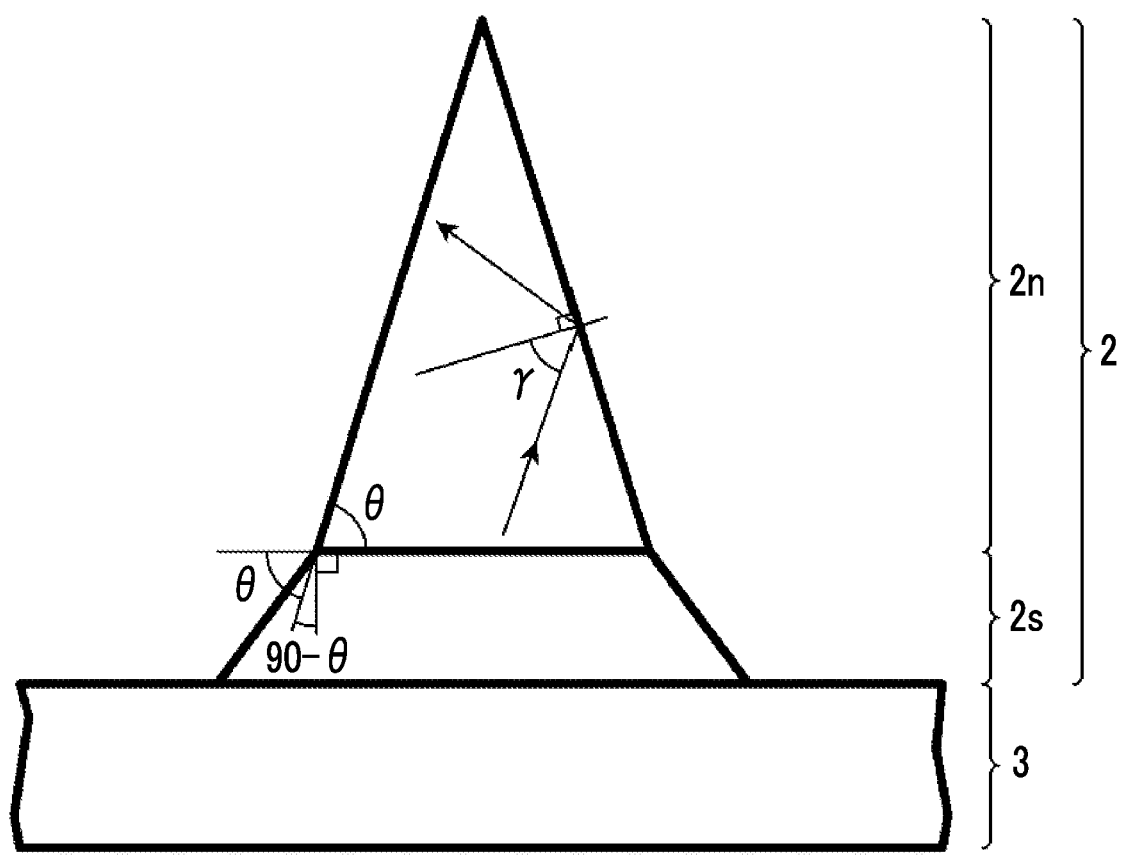
FIG. 13 is a side view illustrating an example of a microneedle having a two-stage structure.

FIG. 13 is a side view illustrating an example of a microneedle having a two-stage structure.

As illustrated in the same figure, the microneedle 2 comprises a needle portion 2n on a tip side; and a pedestal portion 2s on a base side. The needle portion 2n is a portion punctured into the skin and has a conical shape. The pedestal portion 2s is a portion that supports the needle portion 2n on the sheet 3 and has a truncated cone shape.

In a case where the microneedle 2 has a multistage structure, the tip portion thereof is set such that the tip portion is irradiated with illumination light under the above-described conditions.

In other words, in a case where the portion constituting the tip of a microneedle is set as a needle portion and the illumination light is parallel light, the illumination light is radiated under conditions in which the incident angle of light onto the bottom surface of the needle portion is 90−θ° or greater and the incident angle of light onto the side surface of the microneedle is less than the critical angle γ.

Further, in a case where the illumination light is diffused light, the illumination light is radiated under conditions in which the intensity of light incident on the bottom surface of the needle portion of the reference microneedle at an incident angle of less than 90−θ° is 1/10 or less of the entire intensity of light incident on the bottom surface of the needle portion of the reference microneedle and the intensity of light incident on the side surface of the needle portion of the reference microneedle at an incident angle greater than or equal to the critical angle γ is 1/10 or less of the entire intensity of light incident on the bottom surface of the needle portion of the reference microneedle.

Here, the angle θ is defined as the inclination angle of light onto the side surface of the needle portion. Further, the bottom surface of the needle portion is defined as the interface between the needle portion and the second step from the tip side. Therefore, in a case of the microneedle having a two-stage structure, the interface between the needle portion 2n and the pedestal portion 2s constitutes the bottom surface of the needle portion.

By radiating the illumination light in the above-described manner, an image of the microneedle array, in which only the tip portion of the microneedle 2 is darkened, even in a case of the microneedle 2 having a multistage structure can be obtained.

EXPLANATION OF REFERENCES

1: microneedle array
2: microneedle
2a: bottom surface of microneedle
2b: side surface of microneedle
2n: needle portion of microneedle
2s: pedestal portion of microneedle
2x: reference microneedle
2xa: bottom surface of reference microneedle
2xb: side surface of reference microneedle
3: sheet
3A: first surface of sheet
3B: second surface of sheet
10: microneedle array imaging device
20: support portion
22: stage
22A: placement surface of stage
24: opening portion of stage
30: illumination unit
32: parallel light irradiation unit
40: imaging section
42: imaging unit
44: imaging lens
46: camera
50: microneedle array inspection device
52: inspection unit
100: microneedle array imaging device
130: illumination unit
134: diffused light irradiation unit
134A: rocking shaft of diffused light irradiation unit
136: light source unit
138: diffusion plate
200: microneedle array imaging device
220: support portion
222: stage
222A: placement surface of stage
224: opening portion of stage
230: illumination unit
232: parallel light irradiation unit
234: reflection plate
234A: reflection surface of reflection plate
240: imaging section
242: imaging unit
244: lens
244A: half mirror
246: camera
300: microneedle array imaging device
330: illumination unit
332: illumination light irradiation unit
334: diffuse reflection plate
334A: diffusion reflection surface
334B: rocking shaft of diffuse reflection plate
A1: arc
A2: arc
L1: optical axis of parallel light irradiation unit
L2: optical axis of imaging lens
LD: irradiation direction of illumination light radiated by illumination unit
M1: material containing drug
M2: material that does not contain drug
O: center of placement surface of stage
OS: emission surface of diffused light
PL2a: normal line drawn on bottom surface of microneedle
PL2b: normal line drawn on side surface of microneedle
SD: imaging direction of microneedle array imaged by imaging section
TRD: incident direction of light that is totally reflected at smallest incident angle
Za: range of light emitted from emission surface
Zb: range where light incident on bottom surface of reference microneedle at incident angle of less than 90−θ° is emitted
Zc: range where light incident on side surface of reference microneedle at incident angle greater than or equal to critical angle is emitted α: incident angle of light onto bottom surface of microneedle
β: incident angle of light onto side surface of microneedle
γ: critical angle
δ: incident angle at which light incident on side surface of reference microneedle at critical angle is incident on bottom surface of reference microneedle
θ: inclination angle of side surface with respect to bottom surface of microneedle
ψ: axis

What is claimed is:

1. A microneedle array imaging device comprising:
a light source which irradiates a surface on a side opposite to a surface on which a plurality of microneedles whose inclination angle of a side surface with respect to a bottom surface is θ° are arranged on a sheet to form a microneedle array, with parallel light as illumination light; and
a camera which images the microneedle array from a side of the surface on which the microneedles are arranged,
wherein the illumination unit irradiates the surface with the illumination light under conditions in which an incident angle of light onto the bottom surface of the microneedle is 90-θ° or greater and an incident angle of light onto the side surface of the microneedle is less than a critical angle, wherein the critical angle is a smallest angle at which a total reflection occurs on the side surface of the microneedle and is between a direction of the incident angle of light and a normal line drawn on the side surface of the microneedle.

2. The microneedle array imaging device according to claim 1,
wherein the light source irradiates the surface with the illumination light under conditions in which an incident angle of light onto the bottom surface of the microneedle is 90-θ° or greater and an incident angle of light onto the side surface of the microneedle is less than 46°.

3. The microneedle array imaging device according to claim 1,
wherein the camera images the microneedle array under conditions in which a direction in which the microneedle array is imaged becomes parallel to a direction in which the surface is irradiated with the illumination light.

4. The microneedle array imaging device according to claim 1,
wherein the light source comprises:
a light source which emits parallel light from a side of the surface on which the microneedles are arranged toward the microneedle array; and
a reflection plate which reflects the light transmitted through the microneedle array and irradiates the surface on the side opposite to the surface on which the microneedles are arranged with the illumination light.

5. A microneedle array imaging device comprising:
a light source which irradiates a surface on a side opposite to a surface on which a plurality of microneedles whose inclination angle of a side surface with respect to a bottom surface is θ° are arranged on a sheet to form a microneedle array, with illumination light; and
a camera which images the microneedle array from a side of the surface on which the microneedles are arranged,
wherein, the illumination unit irradiates the surface with the illumination light under conditions in which the intensity of light incident on the bottom surface of the reference microneedle at an incident angle of less than 90-θ° is 1/10 or less of the entire intensity of the light incident on the bottom surface of the reference microneedle and the intensity of light incident on the side surface of the reference microneedle at an incident angle greater than or equal to a critical angle is 1/10 or less of the entire intensity of the light incident on the bottom surface of the reference microneedle, wherein the critical angle is a smallest angle at which a total reflection occurs on the side surface of the microneedle and is between a direction of the incident angle of light and a normal line drawn on the side surface of the microneedle.

6. The microneedle array imaging device according to claim 5,
wherein the light source irradiates the surface with diffused light as illumination light.

7. The microneedle array imaging device according to claim 6,
wherein the emission surface is disposed perpendicularly to the sheet.

8. The microneedle array imaging device according to claim 6,
wherein the camera images the microneedle array in a direction inclined with respect to the sheet.

9. The microneedle array imaging device according to claim 6,
wherein the light source comprises:
a light source which emits light from a side of the surface on which the microneedles are arranged toward the microneedle array; and
a diffusion reflection plate which diffuses and reflects the light transmitted through the microneedle array and irradiates the surface on the side opposite to the surface on which the microneedles are arranged with the illumination light.

10. A microneedle array inspection device comprising:
the microneedle array imaging device according to claim 1; and
a hardware processor configured to acquire an image captured by the camera, and analyzes the obtained image to inspect the microneedle array.

11. A microneedle array inspection device comprising:
the microneedle array imaging device according to claim 6; and
a hardware processor configured to acquire an image captured by the microneedle array imaging device, and analyzes the obtained image to inspect the microneedle array.

12. A microneedle array imaging method comprising:
irradiating a surface on a side opposite to a surface on which a plurality of microneedles whose inclination angle of a side surface with respect to a bottom surface is θ° are arranged on a sheet to form a microneedle array, with parallel light as illumination light; and
imaging the microneedle array from a side of the surface on which the microneedles are arranged,
wherein the surface is irradiated with the illumination light under conditions in which an incident angle of light onto the bottom surface of the microneedle is 90-θ° or greater and an incident angle of light onto the side surface of the microneedle is less than a critical angle, wherein the critical angle is a smallest angle at which a total reflection occurs on the side surface of the microneedle and is between a direction of the incident angle of light and a normal line drawn on the side surface of the microneedle.

13. A microneedle array imaging method comprising:
irradiating a surface on a side opposite to a surface on which a plurality of microneedles whose inclination angle of a side surface with respect to a bottom surface is θ° are arranged on a sheet to form a microneedle array, with illumination light; and
imaging the microneedle array from a side of the surface on which the microneedles are arranged,
wherein, the surface is irradiated with the illumination light under conditions in which the intensity of light incident on the bottom surface of the reference microneedle at an incident angle of less than 90-θ° is 1/10 or less of the entire intensity of the light incident on the bottom surface of the reference microneedle and the intensity of light incident on the side surface of the reference microneedle at an incident angle greater than or equal to a critical angle is 1/10 or less of the entire intensity of the light incident on the bottom surface of the reference microneedle, wherein the critical angle is a smallest angle at which a total reflection occurs on the side surface of the microneedle and is between a direction of the incident angle of light and a normal line drawn on the side surface of the microneedle.

14. A microneedle array inspection method comprising:
acquiring an image captured using the microneedle array imaging method according to claim 12, and analyzing the obtained image to inspect the microneedle array.

15. A microneedle array inspection method comprising:
acquiring an image captured using the microneedle array imaging method according to claim 13, and analyzing the obtained image to inspect the microneedle array.

* * * * *